United States Patent
Chen et al.

(10) Patent No.: US 12,285,501 B2
(45) Date of Patent: Apr. 29, 2025

(54) COMPOUND TARGETING NOREPINEPHRINE TRANSPORTER

(71) Applicant: Takahiro Higuchi, Wuerzburg (DE)

(72) Inventors: Xinyu Chen, Wuerzburg (DE); Michael Decker, Wuerzburg (DE); Takahiro Higuchi, Wuerzburg (DE)

(73) Assignee: Takahiro Higuchi, Wuerzburg (DE)

( * ) Notice: Subject to any disclaimer, the term of this patent is extended or adjusted under 35 U.S.C. 154(b) by 743 days.

(21) Appl. No.: 17/423,526

(22) PCT Filed: Jan. 9, 2020

(86) PCT No.: PCT/EP2020/050406
§ 371 (c)(1),
(2) Date: Jul. 16, 2021

(87) PCT Pub. No.: WO2020/148154
PCT Pub. Date: Jul. 23, 2020

(65) Prior Publication Data
US 2022/0096667 A1   Mar. 31, 2022

(30) Foreign Application Priority Data
Jan. 17, 2019  (EP) .................... 19152274

(51) Int. Cl.
*A61K 51/04*  (2006.01)
*A61P 9/00*  (2006.01)
*C07B 59/00*  (2006.01)
*C07C 277/08*  (2006.01)
(Continued)

(52) U.S. Cl.
CPC ............ *A61K 51/04* (2013.01); *A61P 9/00* (2018.01); *C07B 59/002* (2013.01); *C07C 277/08* (2013.01); *C07C 279/08* (2013.01); *C07D 251/08* (2013.01); *C07B 2200/05* (2013.01)

(58) Field of Classification Search
None
See application file for complete search history.

(56) References Cited

U.S. PATENT DOCUMENTS

2014/0328756 A1\* 11/2014 Radeke ............ A61K 51/0497
424/1.89

FOREIGN PATENT DOCUMENTS

| WO | 2008/083056 | 7/2008 |
| WO | 2013/036869 | 3/2013 |

OTHER PUBLICATIONS

International Search Report issued Mar. 23, 2020 in PCT/EP2020/050406, 5 pages.
(Continued)

*Primary Examiner* — Michael G. Hartley
*Assistant Examiner* — Kaila A Craig
(74) *Attorney, Agent, or Firm* — Grüneberg and Myers PLLC

(57) ABSTRACT

A compound according to following formula can be prepared,

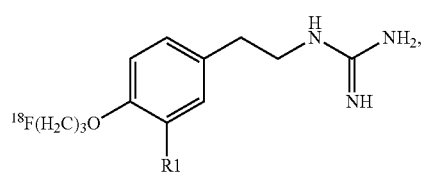

where R1 is an F or I residue.

18 Claims, 11 Drawing Sheets

(51) Int. Cl.
*C07C 279/08* (2006.01)
*C07D 251/08* (2006.01)

(56) References Cited

OTHER PUBLICATIONS

Written Opinion issued Mar. 23, 2020 in PCT/EP2020/050406, 6 pages.
Vaidyanathan et al., "*Sythesis and evaluation of 4-[$^{18}F$]fluoropropoxy-3-iodobenzylguanidine ([$^{18}F$]FPOIBG): A novel 18F-labeled analogue of MIBG*," Nuclear Medicine and Biology 42 (2015) 673-684.
Werner et al., "*Retention Kinetics of the $^{18}F$-Labeled Sympathetic Nerve PET Tracer LMI1195: Comparison with 11C-Hydroxyephedrine and $^{123}I$-MIBG*," The Journal of Nuclear Medicine (2015) 1429-1433.
Rainer Wilcken, et al., "Principles and Applications of Halogen Bonding in Medicinal Chemistry and Chemical Biology", Journal of Medicinal Chemistry 2013, Nov. 12, 2012, vol. 56, Issue 4, pp. 1363-1388.
Anna Tutov, et al., "Rationalizing the Binding Modes of PET Radiotracers Targeting the Norepinephrine Transporter", Pharmaceutics, Feb. 17, 2023, vol. 15, 690, pp. 1-15.

\* cited by examiner

Control NET blockade
(PhB 50mg/kgw iv)

5-20min after $^{18}$F-AF78 injection

COMPOUND TARGETING NOREPINEPHRINE TRANSPORTER

CROSS-REFERENCE TO RELATED APPLICATIONS

This application is the National Stage entry under § 371 of International Application No. PCT/EP2020/050406, filed on Jan. 9, 2020, and which claims the benefit of priority to European Application No. 19152274.7, filed on Jan. 17, 2019. The content of each of these applications is hereby incorporated by reference in its entirety.

BACKGROUND OF THE INVENTION

Field of the Invention

The invention concerns a compound, the compound for use in a diagnostic method, the compound for use in a diagnostic method for diagnosing a disorder in generation, degradation, distribution or function of norepinephrine transporter (NET) and a method for synthesizing the compound.

Description of Related Art

Norepinephrine (NE) is a neurotransmitter. Functions of NE comprise a general mobilization of brain and body as well as an increase of heart rate and blood pressure. NET is responsible for the reuptake of NE released into the synaptic cleft into the presynaptic neuron. Therewith, NET regulates concentration of NE in the synaptic cleft. For detecting NET in the human or animal body several tracers that bind to NET and that can be detected in Positron Emission Tomography (PET) have been developed.

WO 2013/036869 A2 discloses compositions, methods and systems for the synthesis and use of imaging agents comprising $^{18}$F. The imaging agent may be used to image an area of interest in a subject, including the heart, cardiovascular system, cardiac vessels, brain and other organs. In certain embodiments the disclosed methods include a method of detecting NET.

From WO 2008/083056 compounds for use as imaging agents within nuclear medicine applications (PET imaging) for imaging of cardiac innervations and methods of synthesis for obtaining these compounds in radiolabeled form are known.

Vaidyanathan G. et al., Nucl Med Biol. 2015 August, 42(8), pages 673 to 684 disclose synthesis and evaluation of 4-[$^{18}$F]fluoropropoxy-3-iodobenzylguanidine.

Werner, R. A., J Nucl Med. 2015 September, 56(9), pages 1429 to 1433 disclose $^{18}$F—N-[3-bromo-4-(3-fluoro-propoxy)-benzyl]-guanidine as PET tracer for noninvasive assessment of sympathetic innervation of the heart.

From Jung, Yong-Woon et al., ACS Chem. Neurosci. 2017, 8, pages 1530 to 1542 radiotracers of cardiac sympathetic innervation are known. The radiotracers are 4-[$^{18}$F]fluoro-m-hydroxyphenethylguanidine ([$^{18}$F]4F-MHPG, [$^{18}$F]1) and its structural isomer 3-[$^{18}$F]fluoro-p-hydroxyphenethylguanidine ([$^{18}$F]3F-PHPG, [$^{18}$F]2) having the following formulae

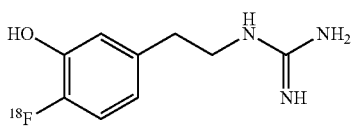

[$^{18}$F]1

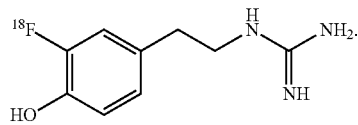

[$^{18}$F]2

According to this document fluorine-18 has a sufficiently long half-life such that the production and distribution of $^{18}$F-labeled radiopharmaceuticals from a central production facility to stand-alone PET imaging centers is feasible. In the document it is further stated that PET studies showed very long neuronal retention times for [$^{18}$F]1 and [$^{18}$F]2 in nonhuman primate myocardium consistent with rapid vesicular uptake and very little diffusion of the tracers from storage vesicles. Furthermore, the guanidine group of the side chain of [$^{18}$F]1 and [$^{18}$F]2 confers stability against neuronal enzymes.

Chen, X. et al., EJNMMI Research (2018) 8:12, pages 1 to 8 discloses $^{18}$F—N-[3-bromo-4-(3-fluoro-propoxy)-benzyl]-guanidine ($^{18}$F-LMI1195) as PET tracer. This tracer is designed for assessment of sympathetic innervation of the heart. It is described that for $^{18}$F-LMI1195 exists an easy and high-yield labeling procedure that is convenient and eligible for commercial preparation and application.

SUMMARY OF THE INVENTION

The problem to be solved by the present invention is to provide an alternative tracer binding to NET, the tracer for use in diagnostic methods as well as a method for synthesizing the tracer.

The problem is solved by the features as described below.
The problem is solved by the features of claims 1, 2, 3 and 6. Embodiments are subject-matter of claims 4, 5 and 7 to 13.

According to the invention a compound according to the following formula

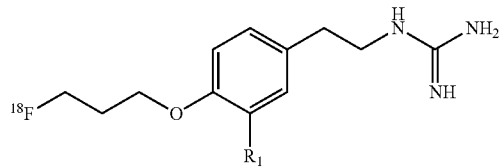

is provided, wherein R1 is an F or an I residue, in particular an F residue.

DETAILED DESCRIPTION OF THE INVENTION

Figure 1:
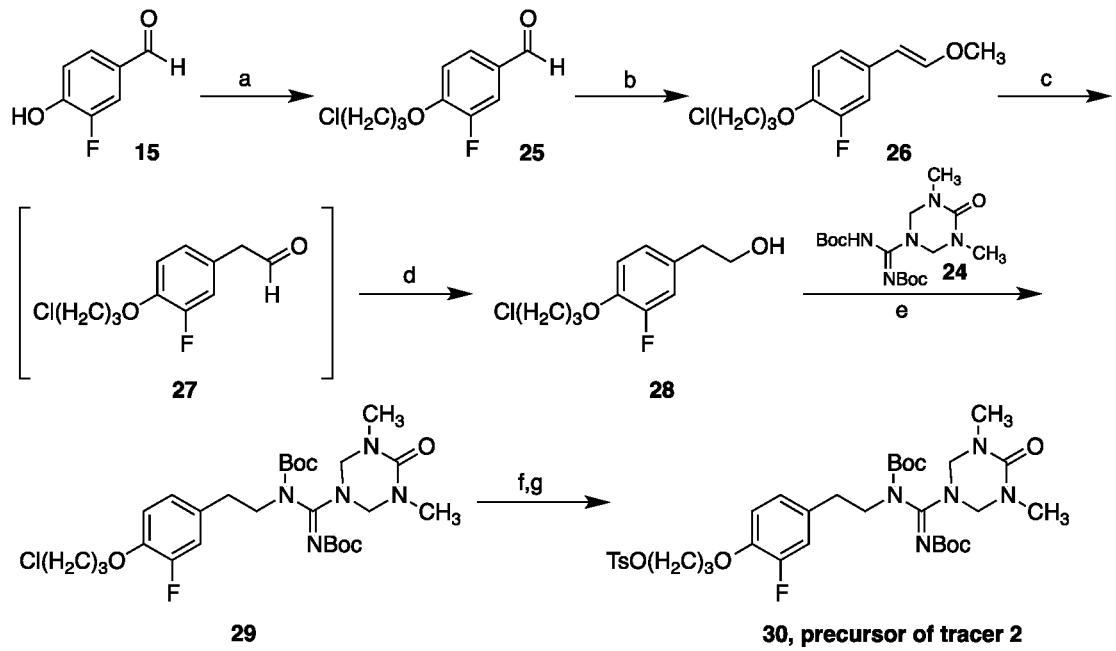
FIG. 1 shows a reaction scheme for synthesis of compound 30 as precursor of tracer 2 (=$^{18}$F-AF78).

The invention further concerns the compound according to the invention for use in a diagnostic method practiced on the living human or animal body, i. e., in vivo. This diagnostic method may be a diagnostic method for diagnosing a disorder in generation, degradation, distribution or function of NET in the human or animal body. The inventors found that the compound according to the invention shows a particular slow uptake and a quick flushing out by the liver in vivo.

The diagnostic method may comprise Positron Emission Tomography (PET) of the human or animal body, to which body the compound has been administered before performing the PET. The disorder in generation, degradation, distribution or function of NET may be associated with a cardiovascular disease, a dysregulated blood pressure, a renal disorder, a neuroendocrine tumor disease or Parkinson's disease.

The invention further concerns a method for synthesizing the compound according to the invention, wherein the method comprises the following steps or consists of the following steps:

a) Removing the methyl group of the following compound 14

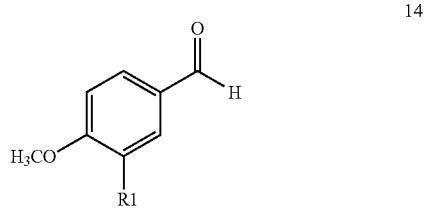

from this compound to receive the following compound 15

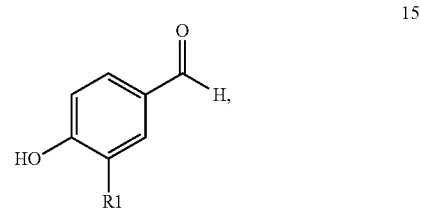

wherein R1 is a halogen residue, b) chloroalkylation of compound 15 by use of 1-chloro-3-iodopropane to receive the following compound 25

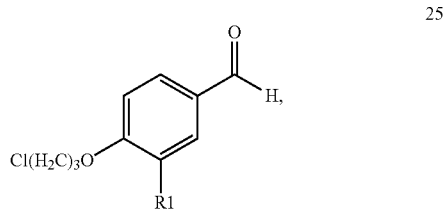

c) performing a Wittig reaction with compound 25 by use of a (methoxymethyl)triphenylphosphonium halide and potassium tert-butoxide or sodium hydride to receive the following compound 26

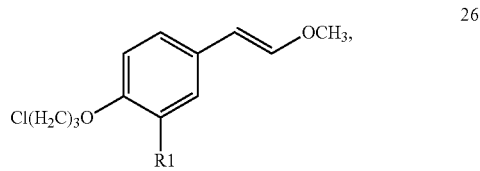

d) reduction of compound 26 in a two step one pot reaction by addition of mercury acetate to allow the formation of an intermediate followed by addition of alkali metal borohydride, in particular sodium borohydride or potassium borohydride, to receive the following compound 28

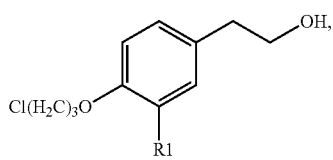

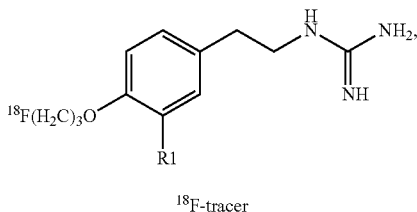

$^{18}$F-tracer e) performing a Mitsunobu reaction with compound 28 in the presence of triphenylphosphine, an azodicarboxylate and the following compound 24

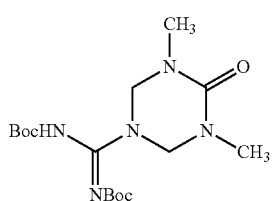

to receive the following compound 29

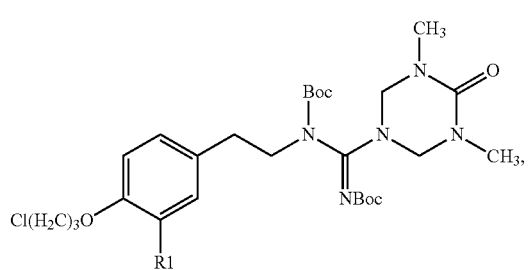

f) replacing the chlorine atom at the terminal of the alkyl chain of the compound resulting from any of steps b) to e) by iodine in a Finkelstein reaction followed by a tosylation using silver p-toluenesulfonate in the dark and if any of steps a) to e) have not been performed up to the present step performing all of steps a) to e) that have not been performed up to the present step to receive the following compound 30

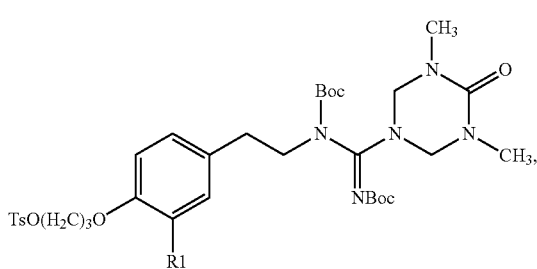

g) radiolabeling compound 30 by a nucleophilic substitution using an alkali metal salt of $^{18}$F, in particular K$^{18}$F, followed by deprotection under acidic condition at a temperature of at least 70° C. to receive the following compound wherein the halogen residue is an F or I residue, in particular an F residue.

If the halogen residue is an F residue the resulting compound is the compound designated as $^{18}$F-AF78 in this application and if the halogen residue is an I residue the resulting compound is the compound designated as $^{18}$F-37 in this application. For both of these compounds efficiency is shown in the embodiments of the invention.

The steps modifying the aldehyde group of compound 14 and groups resulting directly or indirectly from this aldehyde group can be performed partly or completely prior to or after all or of a part of the steps modifying the methoxy group of compound 14 and groups resulting directly or indirectly from this methoxy group. This means that above steps a) to f) can be performed in the given order but also in any other order as long as performing the steps results in compound 30. Performances in different orders are illustrated in the reaction schemes according to FIGS. 1 and 2 and 4 to 6. If steps a) to f) are performed in the given order, all of steps b) to f) are performed in each case with the product of the preceding step which product is identified in the preceding step by a number.

In an embodiment the chlorine atom at the terminal of the alkyl chain of the compound resulting from e) is replaced in step f) by iodine in a Finkelstein reaction.

An advantage of the method according to the invention illustrated in FIG. 1 is that the reaction to extend a benzaldehyde residue by one more methylene groups to achieve a phenethyl moiety which reaction usually takes four steps only takes two steps. These two steps are a Wittig reaction from benzaldehyde 25 to enol ether 26, and a one-pot reaction to phenylethanol 28 through putative intermediate phenylacetaldehyde 27. The intermediate 27 was first planned to be prepared in acidic condition from 26. But after having applied multiple demethylation conditions, such as hydrochloric acid or formic acid, no desired compound could be obtained. Compound 26 decomposes very fast after the addition of acid, even at low temperature and anhydrous condition, and formed the starting material compound 25 again. In the end, a one-pot reaction using mercury (II) acetate is applied as the mercury salt probably stabilizes the putative phenylacetaldehyde intermediate 27, which is not isolated and is directly reduced by addition of NaBH$_4$ in basic solution. As a result, the synthetic scheme is markedly shortened with successful formation of alcohol 28. Though compound 28 is even formed when the alkali metal borohydride is added immediately after addition of mercury acetate, the yield of compound 28 is low in this case. The inventors found that yield is improved when the intermediate 27 has enough time to form between the addition of the mercury acetate and the addition of the reducing agent alkali metal borohydride. If the time between the addition of the mercury acetate and the addition of the reducing agent is too long, hydrolysis back to the benzaldehyde 25 may occur.

The time between the addition of the mercury acetate and the reducing agent may be in the range of 5 minutes to 25 minutes, in particular 6 minutes to 20 minutes, in particular 7 minutes to 15 minutes, in particular 8 minutes to 15 minutes, in particular 9 minutes to 12 minutes. In particular the time between the addition of the mercury acetate and the reducing agent is 10 minutes or about 10 minutes.

Furthermore, the reaction to extend the benzaldehyde residue by one more methylene group should occur at a temperature in the range of 0° C. to 5° C., in particular 0° C. to 4° C., in particular 0° C. to 2° C., in particular 0° C. to 1° C., in particular at a temperature of 0° C.

Compound 24 is used in Mitsunobu reaction to introduce a fully protected guanidine moiety in compound 28 to result in the compound 29. The chlorine atom at the terminal of the alkyl chain is replaced by iodine in a Finkelstein reaction which iodine is subsequently replaced by a tosylate residue for the radiolabeling by reacting with silver tosylate in the dark. The total reaction scheme is illustrated in FIG. 1.

Figure 2:
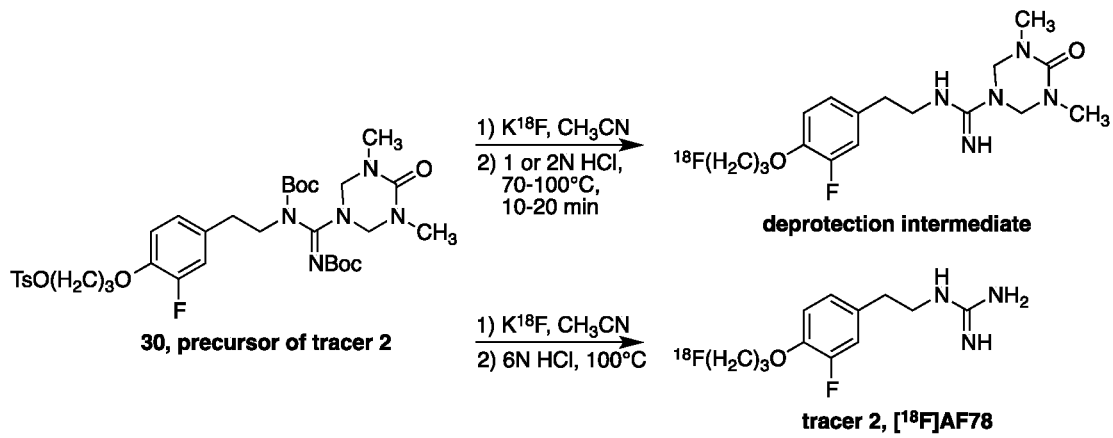
FIG. 2 shows a reaction scheme for synthesis of $^{18}$F-AF78.

Radiofluorination is performed by a nucleophilic method illustrated in FIG. 2. The tosylate moiety is a very good leaving group, which is replaced by [$^{18}$F]fluorine. TLC using autoradiography showed the formation of the fluorinated intermediate before deprotection. The intermediate formed after the removal of both Boc groups still contained the triazinanone structure on the guanidine. This structure turned out to be more stable than expected. Therefore, 6N HCl was used for decomposition of this moiety. The total synthesis time of labeling is approximately 120 min. The average overall radiochemical yield was 7.9±3.1% (decay-corrected based on the starting radioactivity, calculated from 5 times of labeling records) and >97% radiochemical purity.

The (methoxymethyl)triphenylphosphonium halide of step c) may be (methoxymethyl)triphenylphosphonium chloride.

In an embodiment the azodicarboxylate of step e) is diethyl azodicarboxylate (DEAD) or diisopropyl azodicarboxylate (DIAD).

The deprotection under acidic condition of step g) may be performed at a temperature of at most 100° C.

Compound 24 can be synthesized in a method comprising the following steps:

h) Reacting benzyl carbamate, N,N'-dimethylurea and water at a temperature of at least 80° C. to receive the following compound 23

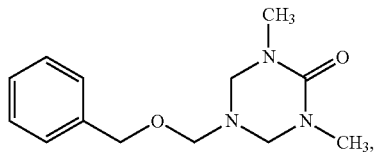

23 i) reacting compound 23 with hydrogen catalyzed by palladium on activated charcoal to receive compound 22

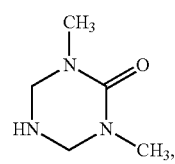

22 j) reacting compound 22 with the following compound 13

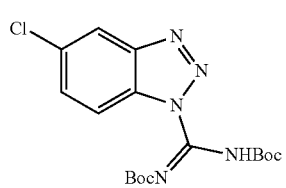

13 in the presence of N,N-diisopropylethylamine (DIPEA) to receive compound 24, wherein Boc is tert-butoxycarbonyl protecting group.

In an embodiment compound 13 of step j) is synthesized by reacting 1,3-bis(tertbutoxycarbonyl)-2-methyl-2-thiopseudourea and 5-chlorobenzotriazole in the presence of mercury (II) chloride (HgCl$_2$).

Figure 3:
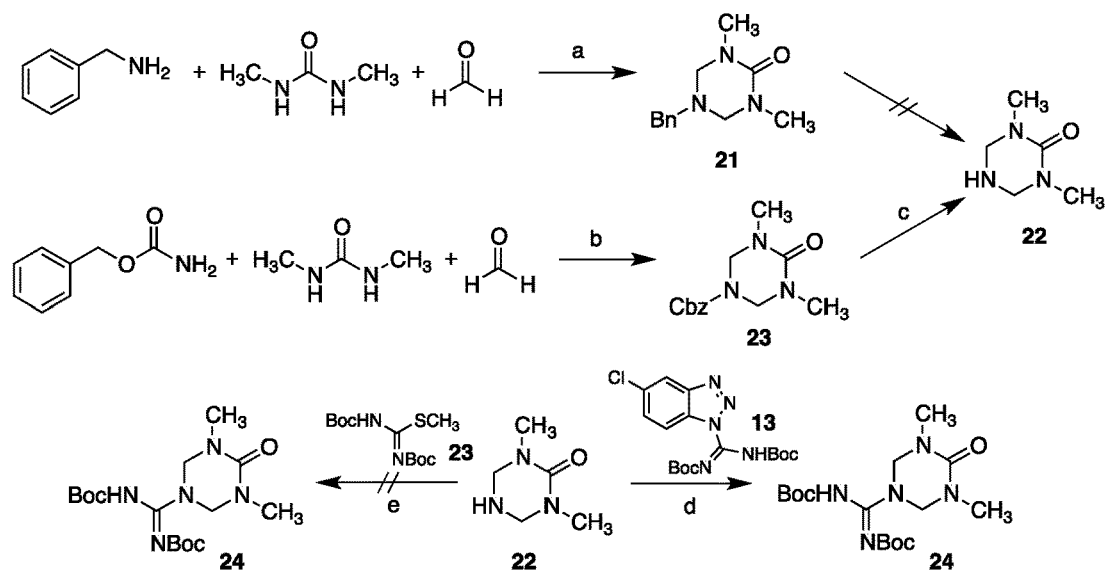
FIG. 3 shows a reaction scheme for synthesis of compound 24.

The total reaction scheme of synthesis of compound 24 is illustrated in FIG. 3. For synthesizing compound 24 the triazinane intermediate 22 is prepared first. When using benzylamine as starting material, the hydrogenation step from resulting compound 21

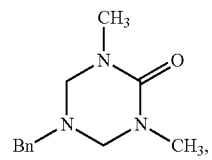

21 wherein Bn is benzyl, to compound 22 would require very high pressure, which is difficult to achieve in lab conditions and also unfeasible for a scaling-up preparation. The improved method of the invention uses benzyl carbamate instead of benzylamine for the preparation of triazinane intermediate 23, which undergoes a much milder condition in the removal of protection group. While forming the fully protected guanidine compound 24 from compound 22, a reaction with pseudourea

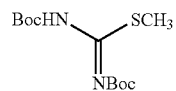

did not work because the triazinane intermediate decomposed. However, the inventors found that compound 24 can be obtained when compound 13 is used instead of the pseudourea.

EMBODIMENTS OF THE INVENTION

Figure 4:
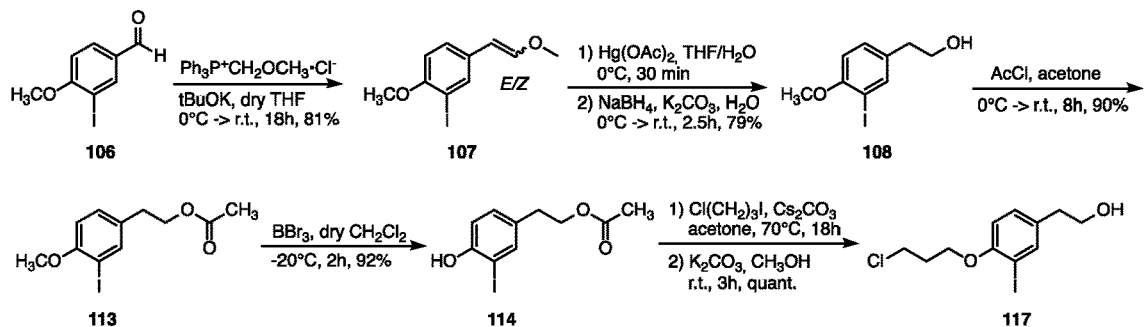
FIG. 4 shows a reaction scheme for synthesis of compound 117.
Figure 5:
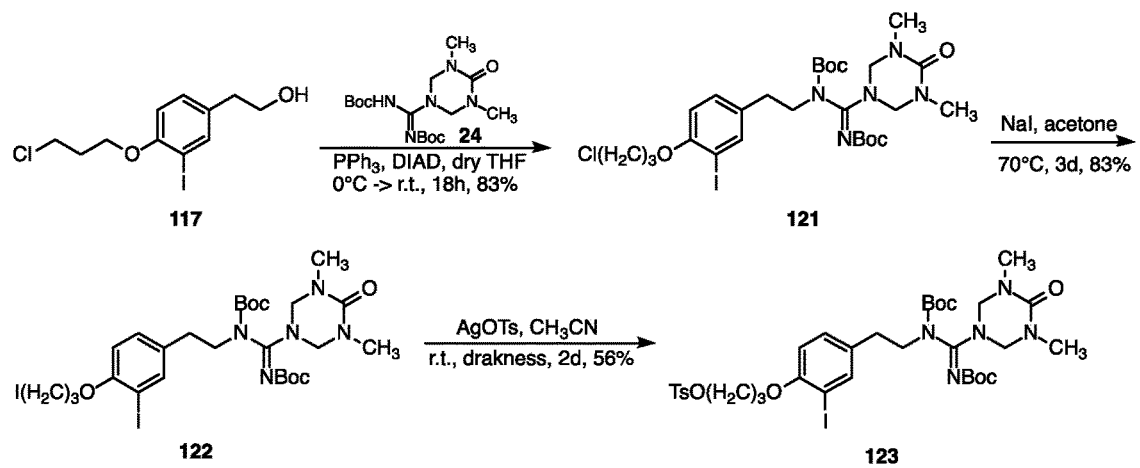
FIG. 5 shows a reaction scheme for synthesis of compound 123 as precursor of tracer $^{18}$F-37.
Figure 6:
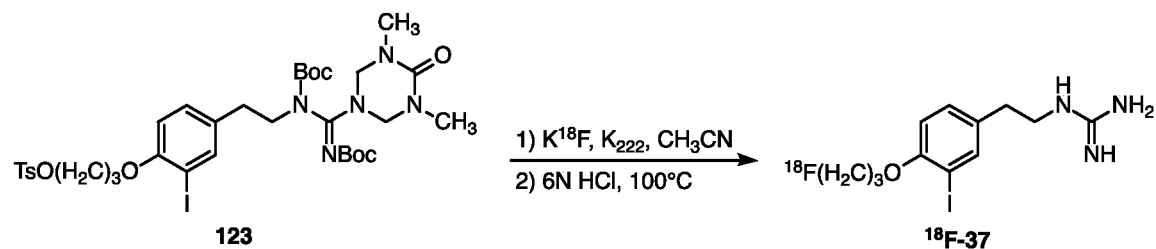
FIG. 6 shows a reaction scheme for synthesis of compound $^{18}$F-37.
Figure 7:
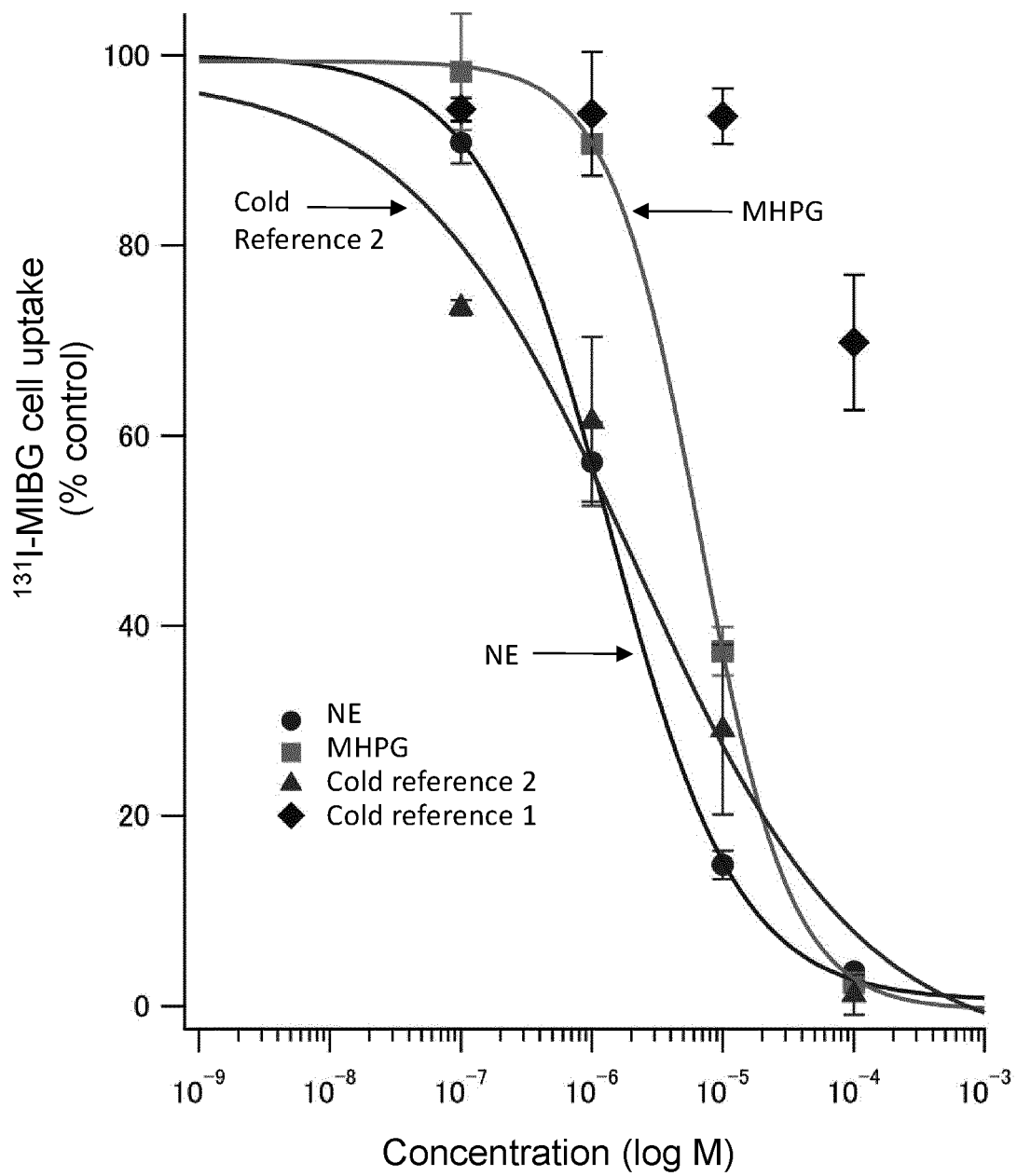
FIG. 7 shows dose-response curves of $^{131}$I-MIBG uptake in SK-N-SH cells in the presence of increasing concentrations of non-radioactive compounds.
Figure 8:
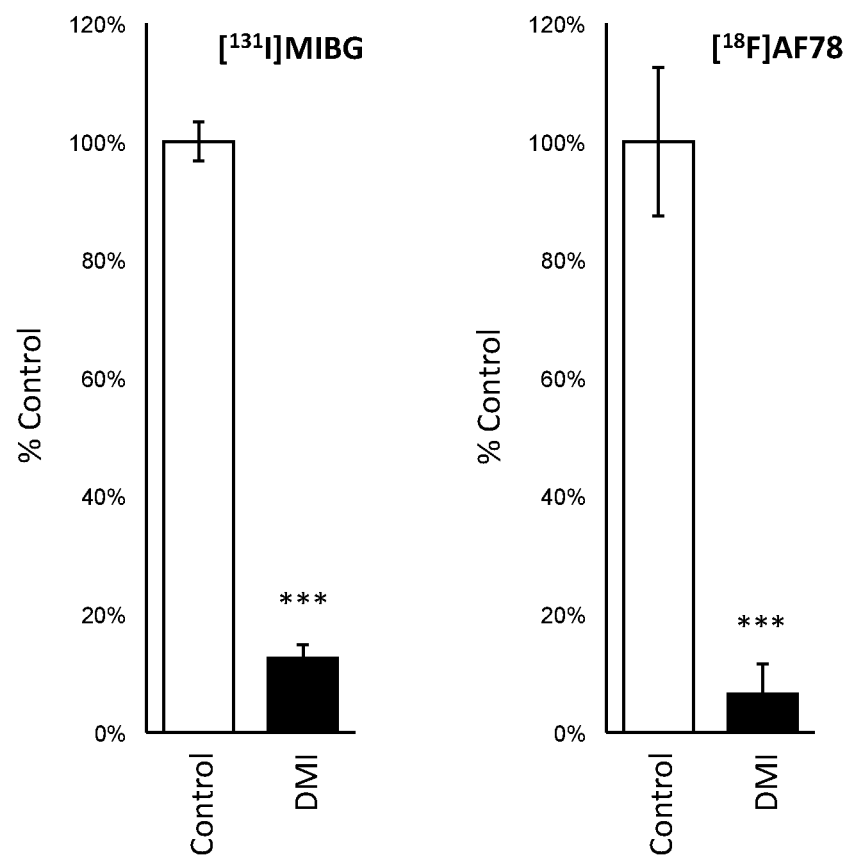
FIG. 8 shows uptake of $^{18}$F-AF78 in SK-N-SH cells with and without NET inhibitor desipramine (DMI).
Figure 9:
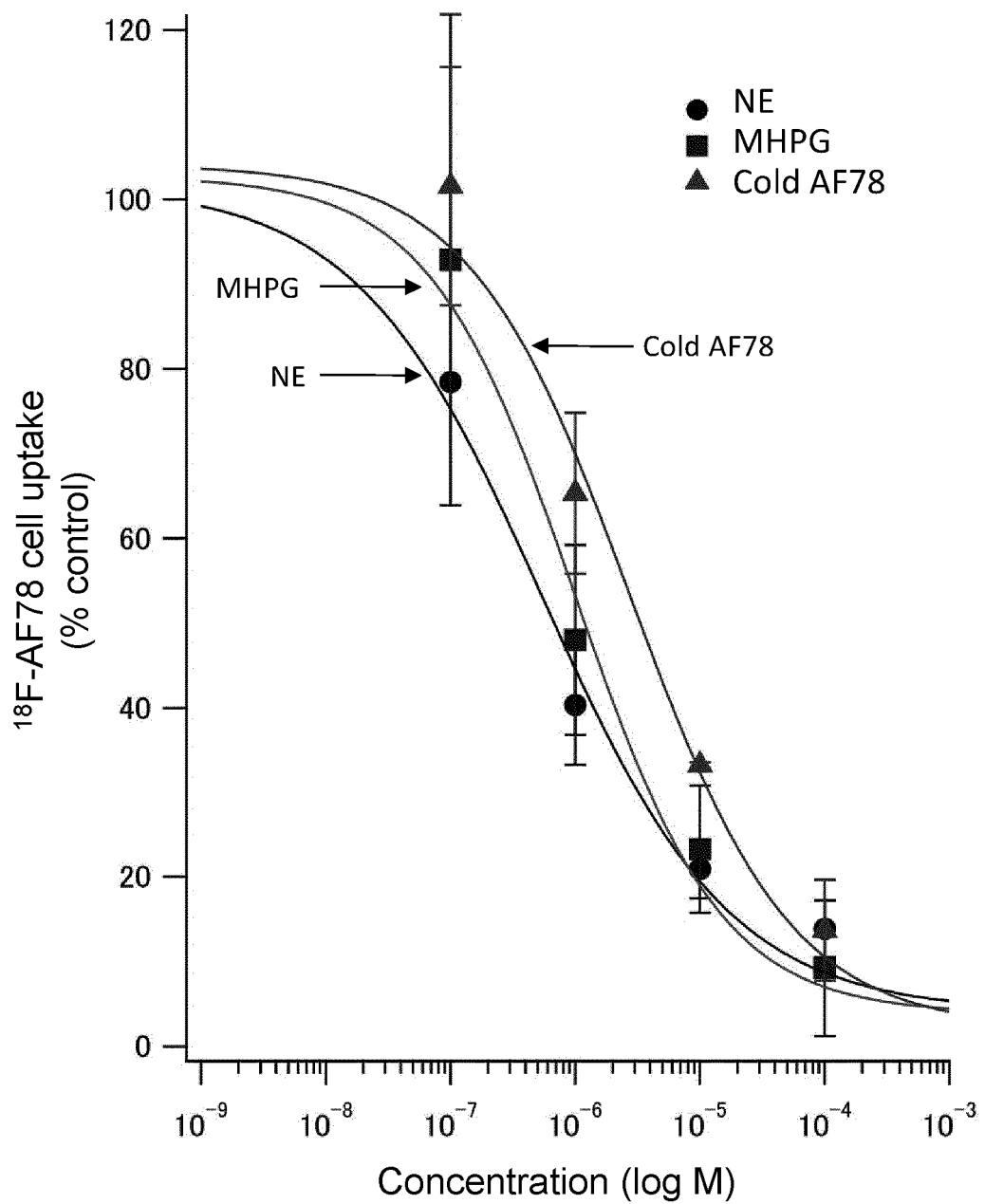
FIG. 9 shows dose-response curves of $^{18}$F-AF78 uptake in SK-N-SH cells in the presence of increasing concentrations of non-radioactive references.
Figure 10:
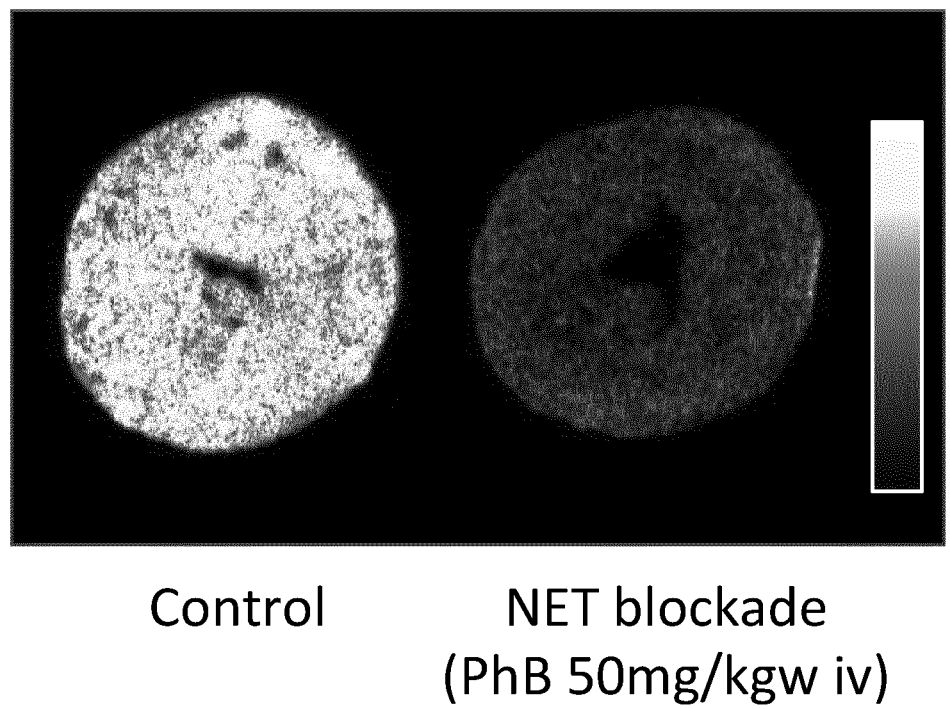
FIG. 10 shows an autoradiography of slices from rats' left ventricular short axis after administration of $^{18}$F-AF78 with and without prior NET blockade.
Figure 11:
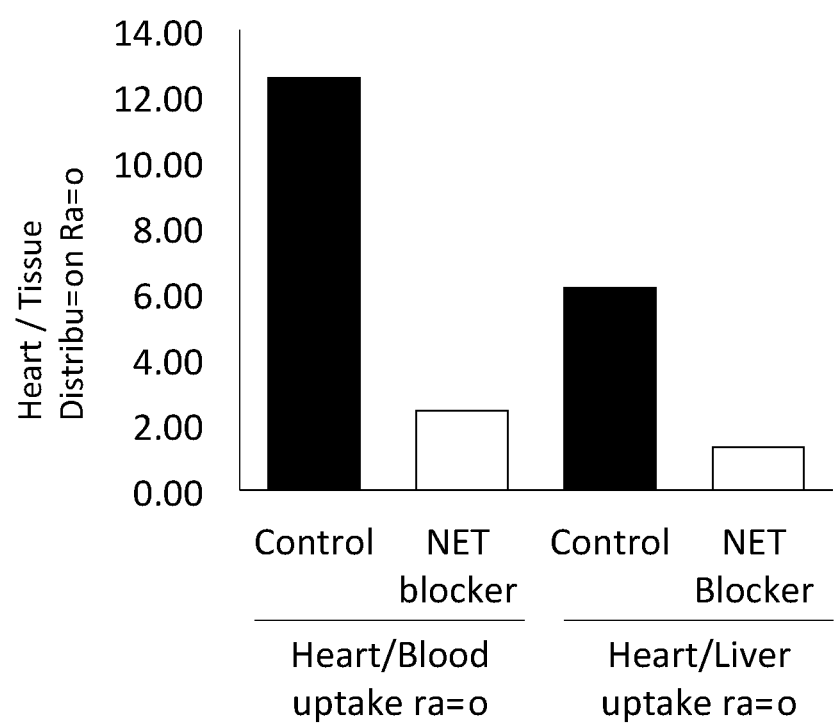
FIG. 11 shows results of a tissue distribution study after administration of $^{18}$F-AF78 with and without prior NET blockade.
Figure 12:
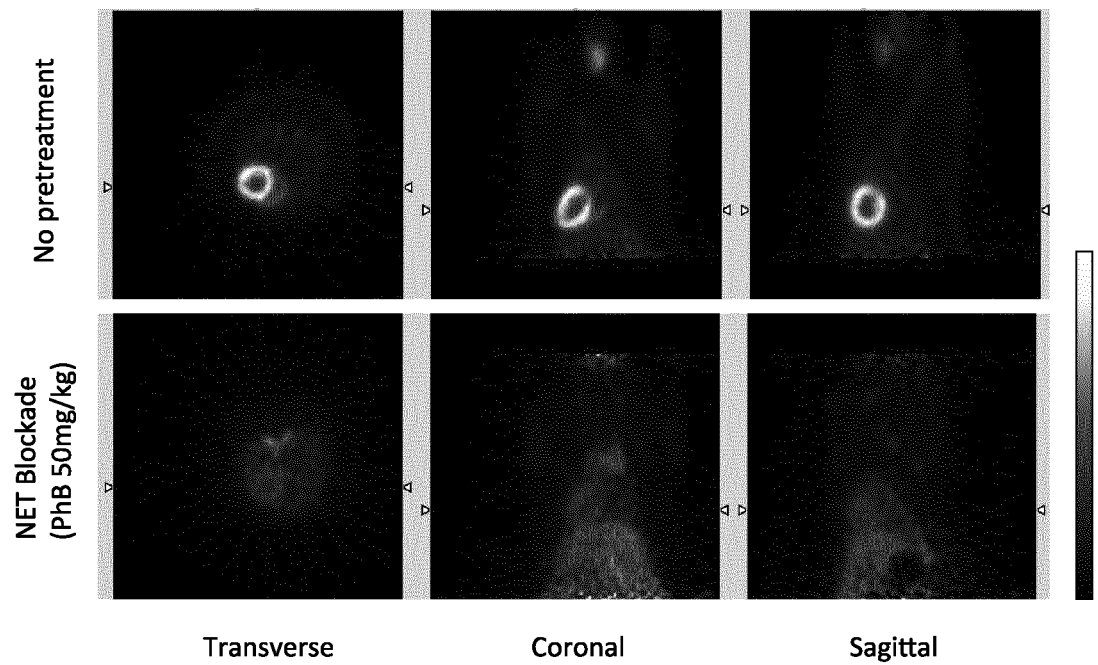
FIG. 12 shows static PET images of cardiac uptake of $^{18}$F-AF78 in healthy rats with and without prior NET blockade.
Figure 13:
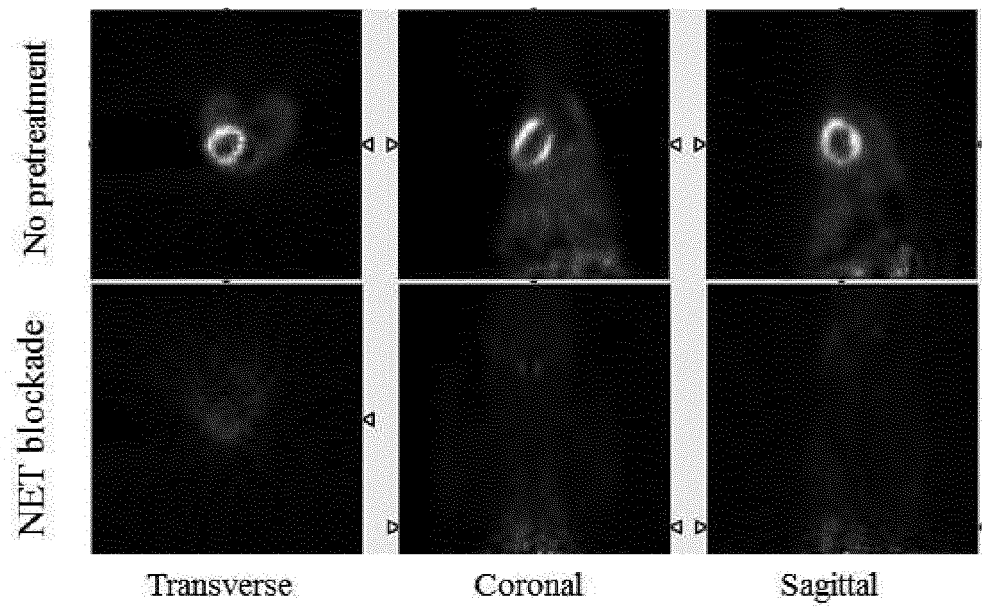
FIG. 13 shows static PET images of cardiac uptake of $^{18}$F-37 in healthy rats with and without prior NET blockade.
Figure 14:
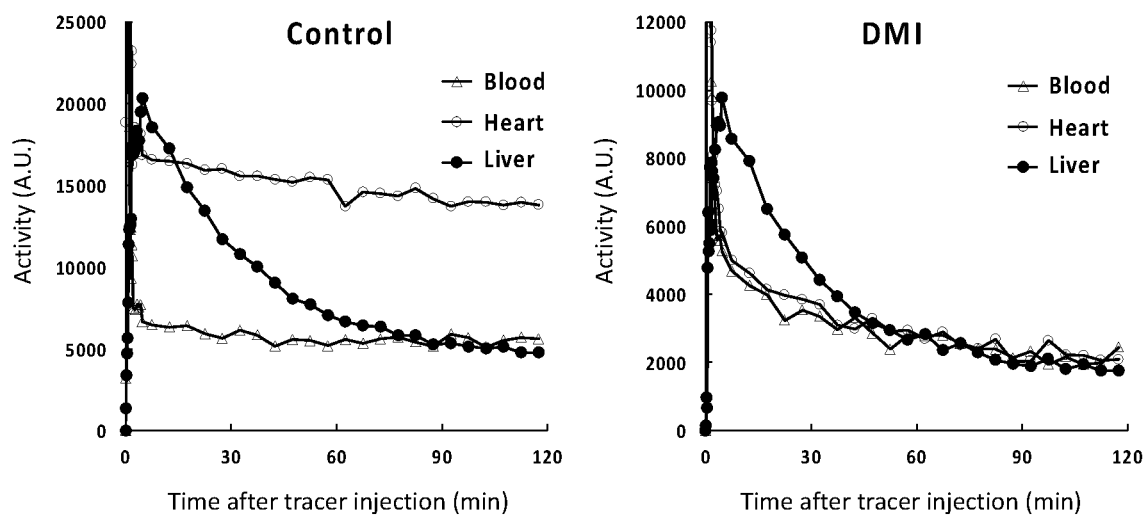
FIG. 14 shows time-activity curves of $^{18}$F-AF78 generated from dynamic PET images in a control monkey with and without prior NET blockade.
Figure 15:
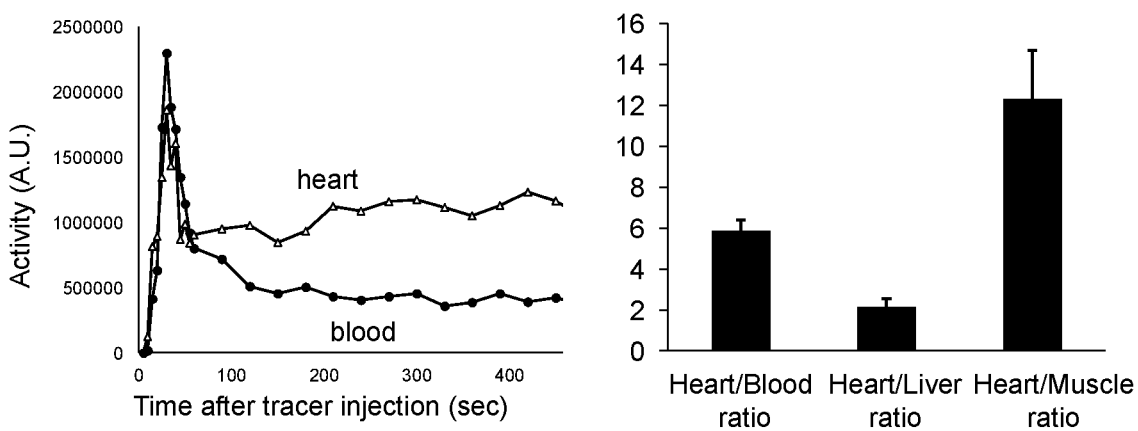
FIG. 15 shows time-activity curves of $^{18}$F-37 generated from dynamic PET images in rat (left panel) and results of biodistribution studies in rats (n=4) showing heart-to-blood (H/B), heart-to-liver (H/L) and heart-to-muscle ratios (H/M) after 10 min of tracer injection (right panel).
Figure 16:
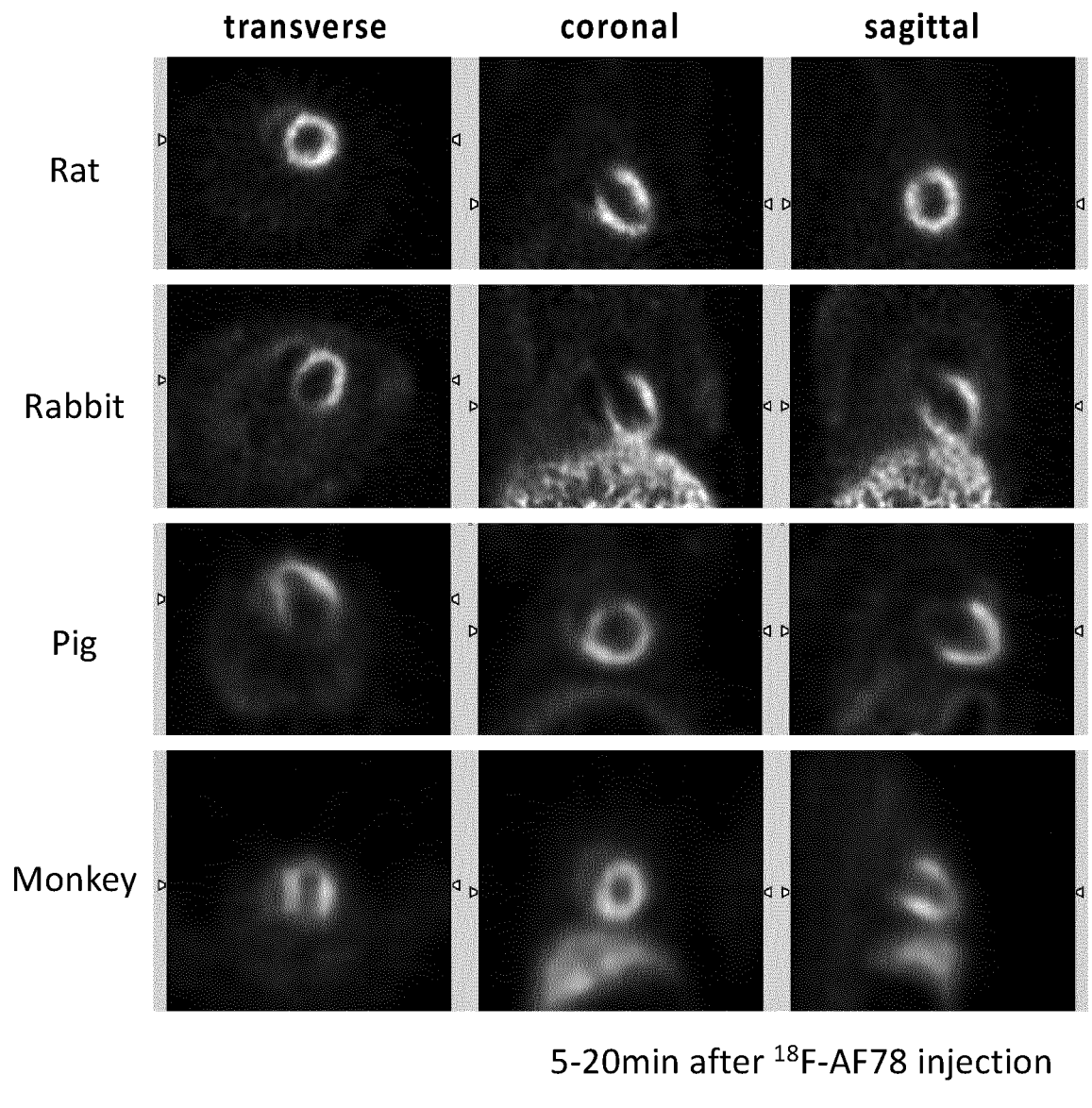
FIG. 16 shows static PET images of cardiac uptake of $^{18}$F-AF78 in healthy rats, rabbits, pigs and monkeys.
Figure 17:
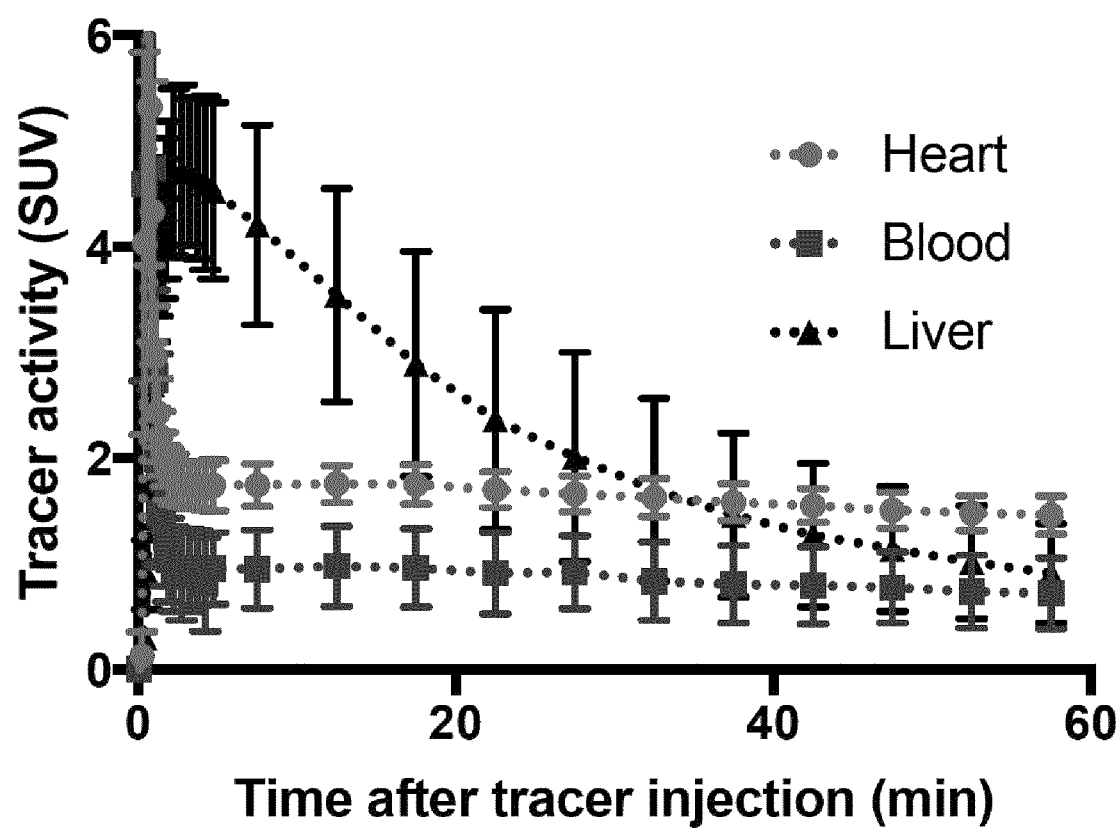
FIG. 17 show the results of a biodistribution study with $^{18}$F-A78 in monkey.
Figure 18:
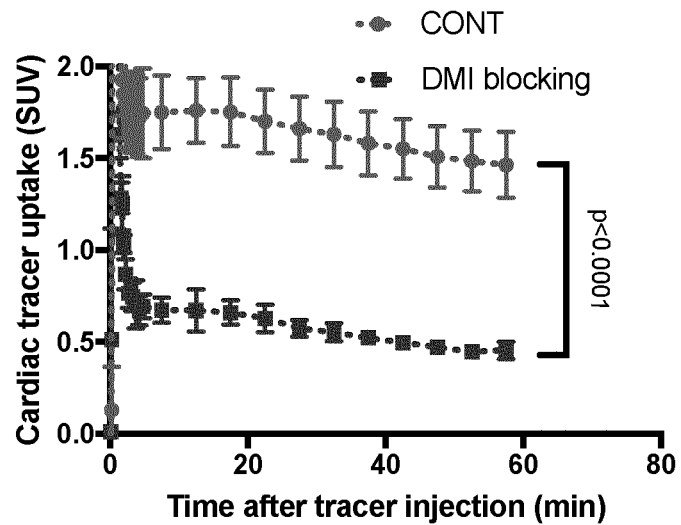
FIG. 18 show the results of a kinetic study performed with $^{18}$F-AF78 in monkeys' hearts. Top panel shows the cardiac tracer uptake with (DMI blocking) and without (CONT) the pretreatment of NET blocker desipramine (DMI). Middle panel shows the tracer uptake with DMI chase (DMI injection after tracer administration) compared with control (CONT). Lower panel shows the tracer uptake with tyramine chase (TYR chase, tyramine, a catecholamine releasing agent, injected after tracer administration) compared with control (CONT).
Figure 18:
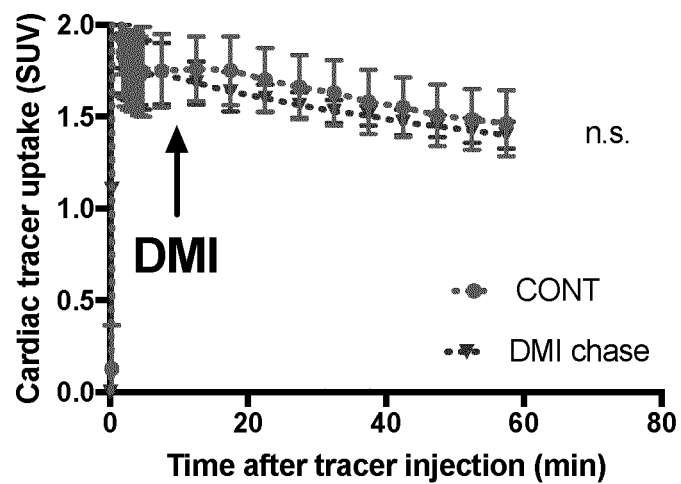
Figure 18:
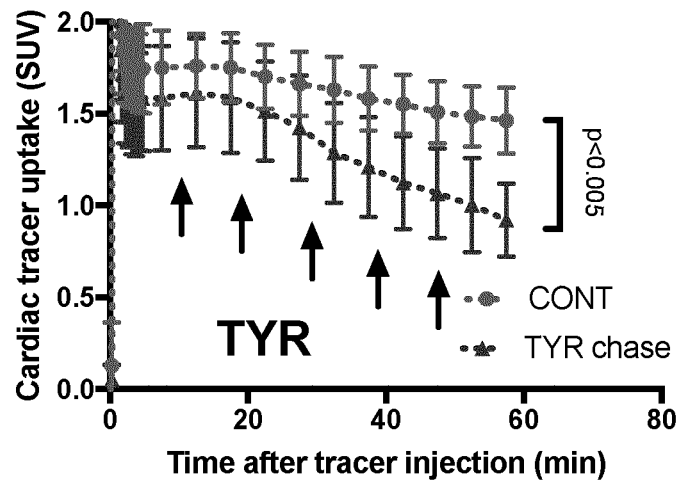

FIG. 1 shows a reaction scheme for synthesis of compound 30 as precursor of tracer 2 (=$^{18}$F-AF78), FIG. 2 shows a reaction scheme for synthesis of $^{18}$F-AF78, FIG. 3 shows a reaction scheme for synthesis of compound 24, FIG. 4 shows a reaction scheme for synthesis of compound 117, FIG. 5 shows a reaction scheme for synthesis of compound 123 as precursor of tracer $^{18}$F-37, FIG. 6 shows a reaction scheme for synthesis of compound $^{18}$F-37, FIG. 7 shows dose-response curves of $^{131}$I-MIBG uptake in SK-N-SH cells in the presence of increasing concentrations of non-radioactive compounds, FIG. 8 shows uptake of $^{18}$F-AF78 in SK-N-SH cells with and without NET inhibitor desipramine (DMI), FIG. 9 shows dose-response curves of $^{18}$F-AF78 uptake in SK-N-SH cells in the presence of increasing concentrations of non-radioactive references, FIG. 10 shows an autoradiography of slices from rats' left ventricular short axis after administration of $^{18}$F-AF78 with and without prior NET blockade, FIG. 11 shows results of a tissue distribution study after administration of $^{18}$F-AF78 with and without prior NET blockade, FIG. 12 shows static PET images of cardiac uptake of $^{18}$F-AF78 in healthy rats with and without prior NET blockade, FIG. 13 shows static PET images of cardiac uptake of $^{18}$F-37 in healthy rats with and without prior NET blockade, FIG. 14 shows time-activity curves of $^{18}$F-AF78 generated from dynamic PET images in a control monkey with and without prior NET blockade, FIG. 15 shows time-activity curves of $^{18}$F-37 generated from dynamic PET images in rat (left panel) and results of biodistribution studies in rats (n=4) showing heart-to-blood (H/B), heart-to-liver (H/L) and heart-to-muscle ratios (H/M) after 10 min of tracer injection (right panel), FIG. 16 shows static PET images of cardiac uptake of $^{18}$F-AF78 in healthy rats, rabbits, pigs and monkeys, FIG. 17 shows the results of a biodistribution study with $^{18}$F-AF78 in monkey and FIG. 18 shows the results of a kinetic study performed with $^{18}$F-AF78 in monkeys' hearts. Top panel shows the cardiac tracer uptake with (DMI blocking) and without (CONT) the pretreatment of NET blocker desipramine (DMI). Middle panel shows the tracer uptake with DMI chase (DMI injection after tracer administration) compared with control (CONT). Lower panel shows the tracer uptake with tyramine chase (TYR chase, tyramine, a catecholamine releasing agent, injected after tracer administration) compared with control (CONT).

SYNTHESIS OF THE COMPOUND ACCORDING TO THE INVENTION

The conditions of the synthesis according to FIG. 1 were as follows:
(a) 1-chloro-3-iodopropane, $K_2CO_3$, acetone, 60° C., 14 h, 87%; (b) (methoxymethyl)triphenylphosphonium chloride, potassium tert-butoxide (KOtBu), THF, 0° C.→r.t., 24 h, 50%; (c) Hg(OAc)$_2$, THF, H2O, 0° C., 15 min; (d) NaBH$_4$, $K_2CO_3$, $H_2O$, 0° C., 30 min, 68%; (e) compound 24, triphenylphosphine (PPh$_3$), diisopropyl azodicarboxylate (DIAD), THF, 0° C.→r.t., 16 h, 84%; (f) NaI, acetone, 70° C., 14 h, 99%; (g) silver p-toluenesulfonate, $CH_3CN$, 0° C.→r.t., dark, 72 h, 98%.

Conditions of the synthesis according to FIG. 3 were as follows:
(a) $H_2O$, 100° C., 14 h, 77%; (b) $CH_3OH$, $H_2O$, 100° C., 14 h, 35%; (c) $H_2$, Pd/C, r.t., 14 h, 88%; (d) compound 13, DIPEA, $CH_3CN$, 50° C., 14 h, 58%; (e) compound 23, HgCl$_2$, DMF, $N_2$, 50° C., 14 h.

Detail of Synthesis of the Compounds of FIGS. 1 to 3

Solvents were dried according to published methods and freshly distilled before use. All other reagents were commercially available compounds and were used without further purification unless noted otherwise. All reactions were carried out under nitrogen atmosphere. $^1$H and $^{13}$C NMR spectral data were obtained from a Bruker Avance II 400 MHz. $^1$H and $^{13}$C NMR chemical shifts (δ) are reported in parts per million (ppm) relative to internal standard TMS and coupling constants (J) are in Hz.

Thin layer chromatography (TLC) was performed on silica gel 60 with a 254 nm fluorescent indicator. UV light or iodine vapor were used for detection. Purity was evaluated via LCMS performed on an LCMS-system by Shimadzu Products, containing a LC20AB liquid chromatograph, an SPD-20A UV/Vis detector and a DGU-20A3R degassing unit. Stationary phase was a Synergi 4 μm fusion-RP (150×4.6 mm) column (Phenomenex, Aschaffenburg, Germany). Mass spectra were obtained by a Shimadzu LCMS-2020 (confirming purity ≥95%). For column chromatography, silica gel 60, 230-400 mesh by Merck was used. For preparative thin layer chromatography, silica gel 60 PF$_{254}$ by Merck was used.

tert-Butyl (E)-((tert-butoxycarbonyl)imino)(5-chloro-1H-benzo[d][1,2,3]triazol-1-yl)methyl)carbamate (13)

1,3-Bis(tert-butoxycarbonyl)-2-methyl-2-thiopseudourea and 5-chlorobenzotriazole were dissolved in dimethylformamide and triethyl amine (0.35 g, 3.45 mol). Mercury(II) chloride (HgCl$_2$) was added and the reaction mixture was stirred at 50° C. for 24 h. The mixture was washed with sodium hydrocarbonate and water and extracted with ethyl acetate (8×50 ml). The combined organic layers were dried over sodium sulfate. The crude product was dissolved in dichloromethane and purified by column (5:1-1:1 petroleum ether:ethyl acetate) to give the target compound 13 as a white solid (0.74 g, 18.7 mmol. 57% yield) which was used in the next step without further purification. ESI-MS (m/z): 396.05 [M+H]$^+$.

3-Fluoro-4-hydroxybenzaldehyde (15)

3-Fluoro-4-methoxybenzaldehyde 14 (5.00 g, 32.5 mmol) was mixed with 48% HBr (30 mL), heated to 140° C. and stirred under argon atmosphere for 3 h. The mixture was diluted with water (150 mL) and extracted with dichloromethane (2×100 mL). The combined organic layers were washed with brine solution and dried over sodium sulfate. The solvent was removed in vacuo to give compound 15 as a brown solid (4.36 g, 30.2 mmol, 97% yield). NMRs are in accordance to literature. (Jiang 2014) ESI-MS (m/z): 141.00 [M+H]$^+$.

5-Benzyl-1,3-dimethyl-1,3,5-triazinan-2-one (21)

Benzylamine (9.81 g, 91.7 mmol) was dissolved in formaldehyde (14.7 g, 183 mmol, 40% aq. solution) and heated to 100° C. under argon atmosphere. N,N'-dimethylurea (8.07 g, 91.7 mmol) was added and the mixture was stirred for 14 h. The mixture was washed with water and extracted with dichloromethane (2×200 mL). The combined organic layers were washed with brine solution and dried over sodium sulfate. The solvent was removed in vacuo and the crude product was purified by column chromatography (1:1 petroleum etherethyl acetate) to give the title compound 21 as yellow crystals (15.5 g, 70.9 mmol, 77% yield). $^1$H NMR (CDCl$_3$, 400 MHz) δ=2.85 (s, 6H), 3.90 (s, 2H), 4.16 (s, 4H), 7.28 (m, 5H) ppm. $^{13}$C NMR (CDCl$_3$, 101 MHz)

δ=32.47, 55.36, 67.72, 127.70, 128.60, 129.11, 137.49, 156.04 ppm. ESI-MS (m/z): 220.10 [M+H]$^+$.

Benzyl 3,5-dimethyl-4-oxo-1,3,5-triazinane-1-carboxylate (23)

Benzyl carbamate (1.00 g, 6.62 mmol) was dissolved in formaldehyde (1.18 g, 14.6 mmol, 40% aq. solution) and methanol. The mixture was heated to 100° C. under argon atmosphere, N,N'-dimethylurea (0.58 g, 6.62 mmol) was added and the mixture was stirred for 14 h. The solvent was removed in vacuo and crude product was washed with water and extracted with dichloromethane (2×200 mL). The combined organic layers were washed with brine solution and dried over sodium sulfate. The solvent was removed in vacuo and the crude product was purified by column chromatography (1:1 petroleum etherethyl acetate, then 25:1 dichloromethane:methanol) to give the title compound 23 as a colourless liquid (0.60 g, 2.29 mmol, 35% yield). $^1$H NMR (CDCl$_3$, 400 MHz) δ=2.79 (s, 6H), 4.62 (s, 4H), 5.09 (s, 2H), 7.26-7.27 (5H) ppm. $^{13}$C NMR (CDCl$_3$, 101 MHz) δ=32.66, 60.34, 68.15, 128.04, 128.40, 128.58, 135.56, 154.39, 156.07 ppm. ESI-MS (m/z): 264.00 [M+H]$^+$.

1,3-Dimethyl-1,3,5-triazinan-2-one (22)

Compound 23 (603 mg, 2.29 mmol) was dissolved in methanol, palladium on activated charcoal (30 mg) was added and the reaction mixture was stirred at r.t. for 14 h under hydrogen atmosphere. The mixture was filtered and the filtrate was concentrated in vacuo to give the title compound 22 as white solid (259 mg, 2.01 mmol, 88% yield). $^1$H NMR (CDCl$_3$, 400 MHz) δ=2.77 (s, 1H), 2.85 (s, 5H), 4.16 (s, 4H) ppm.

tert-Butyl (Z)-(((tert-butoxycarbonyl)imino)(3,5-dimethyl-4-oxo-1,3,5-triazinan-1-yl)methyl)carbamate (24)

To a solution of compound 22 (137 mg, 1.06 mmol) and compound 13 (420 mg, 1.06 mmol) in acetonitrile, DIPEA (274 mg, 2.13 mmol) was added and the mixture was stirred at 50° C. for 14 h. The solvent was removed in vacuo. The residue was diluted with water (50 mL) and extracted with ethyl acetate (2×30 ml) and dichloromethane (2×30 ml). The combined organic phases were washed with brine, dried over sodium sulfate and the solvent was removed in vacuo. The crude product was purified by column chromatography (6:1 then 2:1 petroleum ether:ethyl acetate, 1:1:0.05 petroleum etherethyl acetate:triethylamine) to give the target compound 24 as white crystals (226 mg, 0.61 mmol, 58% yield). $^1$H NMR (CDCl$_3$, 400 MHz) δ=1.47-1.48 (m, 18H), 2.01-2.02 (m, 1H), 2.90-2.91 (m, 6H), 4.69 (s, 6H) ppm. $^{13}$C NMR (CDCl$_3$, 101 MHz) δ=28.16, 33.18, 60.47, 62.31, 81.82, 154.01, 157.30 ppm. ESI-MS (m/z): 372.20 [M+H]$^+$.

4-(3-Chloropropoxy)-3-fluorobenzaldehyde (25)

To a solution of compound 15 (2.50 g, 17.9 mmol) and potassium carbonate (2.71 g, 19.6 mmol) in acetone, 1-chloro-3-iodopropane (3.64 g, 17.9 mmol) was added and the reaction mixture was stirred at 60° C. for 14 h. The solvent was evaporated and the residue was diluted with water (100 mL) and extracted with ethyl acetate (2×50 ml). The combined organic phases were washed with brine and dried over sodium sulfate. The solvent was removed in vacuo and the crude product was purified by column chromatography (5:1 petroleum ether:ethyl acetate). The solvent was removed in vacuo to give compound 25 as a pale-yellow liquid (3.36 g, 15.6 mmol, 87% yield). $^1$H NMR (CDCl$_3$, 400 MHz) δ=2.23-2.32 (m, 2H), 3.74-3.78 (m, 2H), 4.22-4.28 (m, 2H), 7.58-7.80 (m, 3H), 9.85 (s, 1H) ppm. $^{13}$C NMR (CDCl$_3$, 101 MHz) δ=31.98, 41.14, 65.69, 113.62, 113.81, 115.94, 116.15, 123.30, 123.37, 130.20, 130.30, 147.54, 148.66, 150.66-153.12 (J(C-F)=254.4 Hz), 189.96 ppm. ESI-MS (m/z): 217.10 [M+H]$^+$.

(E)-1-(3-Chloropropoxy)-2-fluoro-4-(2-methoxyvinyl)benzene (26)

(Methoxymethyl)triphenylphosphonium chloride (538 mg, 1.57 mmol) was dissolved in dry tetrahydrofuran and cooled to 0° C. Potassium tert-butoxide (228 mg, 2.04 mmol) was added portionwise and the mixture was stirred for 1 h. Compound 25 (200 mg, 1.00 mmol) in dry tetrahydrofuran was added dropwise under cooling and the reaction was warmed to room temperature over night. After mixture was quenched with water, the solvent was removed in vacuo and the residue was diluted with water (100 mL) and extracted with ethyl acetate (2×50 ml). The combined organic phases were washed with brine and dried over sodium sulfate. The solvent was removed in vacuo and the crude product was purified by column chromatography (15:1 petroleum ether:ethyl acetate) to give the target compound 26 as a colorless oil (192 mg, 0.78 mmol, 50% yield). $^1$H NMR (CDCl$_3$, 400 MHz) δ=2.25 (m, 2H), 3.37 (s, 2H), 3.76-3.77 (m, 3H), 4.16 (m, 2H), 5.13-5.14 (d, J=6.9 Hz, 1H), 5.70-5.73 (d, J=13.0 Hz, 0.5H), 6.08-6.10 (d, J=7.0 Hz, 0.5H), 6.87-6.89 (m, 3H) ppm. $^{13}$C NMR (CDCl$_3$, 101 MHz) δ=32.47, 41.52, 41.55, 56.70, 60.78, 66.15, 66.29, 112.69, 112.88, 115.08, 115.10, 115.84, 115.86, 116.02, 116.21, 121.13, 121.17, 147.57, 148.78, 151.91-154.35 (J(C—F)=245.1 Hz), 153.80 ppm.

2-(4-(3-Chloropropoxy)-3-fluorophenyl)ethan-1-ol (28)

Compound 26 (90 mg, 0.37 mmol) was dissolved in tetrahydrofuran and a solution of mercury(II) acetate (129 mg, 0.41 mmol) in water was added under cooling in an ice/water bath. The reaction mixture was stirred for 15 mins and sodium borohydride (56 mg, 1.48 mmol) in a saturated potassium carbonate solution was added dropwise. The reaction mixture was stirred for 30 min, diluted with water and extracted with ethyl acetate (4×10 ml). The combined organic phases were washed with brine and dried over sodium sulfate. The solvent was removed in vacuo and the crude product was purified by column chromatography (4:1 petroleum ether:ethyl acetate) to give the target compound 28 as colorless oil (58.5 mg, 0.25 mmol, 68% yield). $^1$H NMR (CDCl$_3$, 400 MHz) δ=2.22-2.28 (m, 2H), 2.77-2.80 (t, J=6.5 Hz, 2H), 3.75-3.83 (m, 4H), 4.15-4.18 (t, J=5.8 Hz, 2H), 6.91-6.98 (m, 3H) ppm. $^{13}$C NMR (CDCl$_3$, 101 MHz) δ=31.27, 38.82, 41.32, 41.43, 62.64, 65.98, 113.39, 113.46, 116.63, 116.84, 125.48, 125.56, 133.36, 133.39, 144.45, 144.85, 153.22-156.17 (J(C-F)=251.5 Hz) ppm.

tert-butyl (E)-((tert-butoxycarbonyl)imino)(3,5-dimethyl-4-oxo-1,3,5-triazinan-1-yl)methyl)(4-(3-chloropropoxy)-3-fluorophenethyl)carbamate (29)

Compound 28 (72 mg, 0.31 mmol), compound 24 (172 mg, 0.46 mmol) and triphenyl phosphine (122 mg, 0.46 mmol) were dissolved in dry tetrahydrofuran. A solution of DIAD (94 mg, 0.46 mmol) in dry tetrahydrofuran was added dropwise at 0° C. and the reaction mixture was slow warmed up to room temperature and stirred for 16 h. The mixture was diluted with water (40 mL) and extracted with diethyl ether (4×10 ml). The combined organic phases were washed with brine and dried over sodium sulfate. The solvent was removed in vacuo and the crude product was purified by column chromatography (2.5:1.5:0.5 petroleum ether:acetone:ethyl acetate) to give the target compound 29 as a colorless liquid (152 mg, 0.26 mmol, 84% yield). $^1$H NMR (CDCl$_3$, 400 MHz) δ=1.47 (s, 18H), 2.22-2.25 (m, 2H), 2.84 (m, 6H), 3.57 (bs, 4H), 3.74-3.77 (m, 2H), 4.13-4.16 (m, 2H), 4.52 (bs, 4H), 6.89-6.95 (m, 3H) ppm. $^{13}$C NMR (CDCl$_3$, 101 MHz) δ=28.14, 28.25, 41.43, 48.87, 60.49, 61.02, 66.02, 80.84, 83.00, 115.48, 116.55, 116.73, 124.40, 124.43, 131.50, 131.56, 145.60, 145.71, 150.98, 151.52-153.97 (J(C-F)=246.8 Hz), 152.31, 156.98, 158.39 ppm. ESI-MS (m/z): 586.25, 588.25 [M+H]$^+$.

tert-butyl (E)-((tert-butoxycarbonyl)imino)(3,5-dimethyl-4-oxo-1,3,5-triazinan-1-yl)methyl)(3-fluoro-4-(3-odopropoxy)phenethyl)carbamate (30a)

Compound 29 (72 mg, 0.12 mmol) and sodium iodine (37 mg, 0.25 mmol) were dissolved in acetone and the reaction mixture was stirred at 70° C. for 14 h. The mixture diluted with water (40 mL) and extracted with diethyl ether (4×10 ml). The combined organic phases were washed with brine and dried over sodium sulfate. The solvent was removed in vacuo to give the target compound 30a as a yellow liquid (83 mg, 0.12 mmol, 99% yield) and was used directly in the next step without further purification. ESI-MS (m/z): 678.20 [M+H]$^+$, 700.20 [M+Na]$^+$.

(E)-3-(4-(2-(N,N'-bis(tert-butoxycarbonyl)-3,5-dimethyl-4-oxo-1,3,5-triazinane-1-carboximidamido)ethyl)-2-fluorophenoxy)propyl 4-methylbenzenesulfonate (30)

Compound 30a (72 mg, 0.11 mmol) was dissolved in acetonitrile and silver p-toluenesulfonate (148 mg, 0.53 mmol) in darkness at 0° C. The reaction mixture was stirred at room temperature for 72 h. The crude product was diluted with water (40 mL) and extracted with ethyl acetate (4×10 ml). The combined organic phases were washed with brine and dried over sodium sulfate. The solvent was removed in vacuo to give the target compound 30 as a yellow liquid (75 mg, 0.10 mmol, 98% yield). $^1$H NMR (CDCl$_3$, 400 MHz) δ=1.48 (s, 18H), 2.11-2.14 (m, 2H), 2.14 (s, 3H), 2.85 (s, 6H), 3.85 (bs, 4H), 3.89-4.01 (m, 2H), 4.22-4.25 (m, 2H), 4.55 (bs, 4H), 6.77-6.93 (m, 3H), 7.26-7.28 (m, 2H), 7.75-7.77 (d, J=8.3 Hz) ppm. $^{13}$C NMR (CDCl$_3$, 101 MHz) δ=28.15, 28.26, 29.05, 29.80, 33.22, 33.66, 60.50, 61.20, 64.87, 66.98, 80.93, 83.06, 115.32, 116.49, 116.67, 124.42, 127.98, 129.95, 131.55, 132.92, 144.92, 145.36, 145.47, 151.37, 152.28, 153.82, 156.95 ppm. ESI-MS (m/z): 722.35 [M+H]$^+$, 744.30 [M+Na]$^+$.

Radiochemistry $^{18}$F-Fluoride trapped on a Sep-Pak QMA cartridge was first washed with distilled water (3 mL) to remove $^{18}$O-water. $^{18}$F-Fluoride was then eluted from the cartridge with K$_2$CO$_3$ solution (0.3 mL, 23 μmol/mL) into a vial that contains Kryptofix$_{222}$ (22.5 mg, 59.7 μmol). Acetonitrile (0.5 mL×4) was added to the vial, and the solution was dried azeotropically under argon at 120° C. Labeling is carried out by adding the solution of the precursor (4.8 mg) in dry acetonitrile (0.3 mL), followed by heating and stirring at 110° C. for 10 min. Hydrochloric acid (6N, 0.3 mL) was added to the reaction mixture, and the reaction continued for 20 min at 100° C. The mixture was cooled, diluted with 1 mL of a mixture solution of water and acetonitrile (1:1), and applied to the semi-preparative HPLC for purification. HPLC condition: Column: 9.4×250 mm 5-micron ZORBAX Eclipse XDB-C18 (P.N.: 990967-202). Mobile phase: Phase A: Millipore water with 0.1% formic acid; Phase B: Methanol with 0.1% formic acid. Condition: 0-20 min, 30%-60% B, 20-22 min 60-100% B, 22-50 min 100% B; Flow rate 3 mL/min. Condition of autoradiography: TLC with normal phase silica gel 60. Solvent system: 3 mL methanol+20 μL formic acid, R$_f$: 0.6. $^{131}$I-MIBG was purchase from GE Healthcare (Freiburg im Breigau, Germany) and used within 2 h after calibration time. $^{131}$I-MIBG was chosen instead of $^{123}$I-MIBG due to its relative longer half-life, which is convenient for research purposes and financial reasons.

Detail of Synthesis of the Compounds of FIGS. 4 to 6

(E/Z)-2-odo-1-methoxy-4-(2-methoxyvinyl)benzene C$_{10}$H$_{11}$O$_2$I (107)

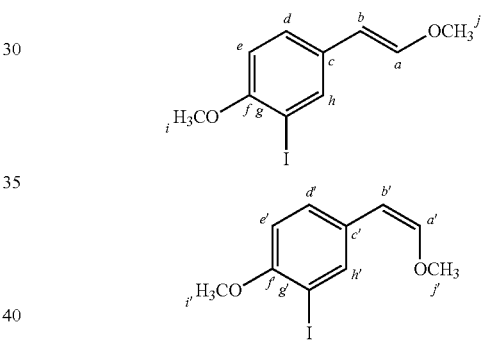

(Methoxymethyl)triphenylphosphonium chloride (3.94 g, 11.50 mmol, 1.50 equiv.) was dissolved in dry tetrahydrofuran (60 mL) under inert gas atmosphere and potassium tert-butoxide (1.47 g, 13.13 mmol, 1.71 equiv.) was added at 0° C. The reaction mixture was stirred for 2 min at 0° C. before commercially available 3-iodo-4-methoxybenzaldehyde 106 (2.01 g, 7.66 mmol, 1.00 equiv.) was added. The solution was stirred at room temperature for 18 h and evaporated to dryness. The residue was partitioned between in ethyl acetate (50 mL) and water (50 mL) followed by layer separation. The aqueous layer was extracted with ethyl acetate (2×50 mL) and the combined organic layers were washed with brine (1×100 mL) and dried over sodium sulfate. The solvent was removed under reduced pressure and the crude material was purified by column chromatography (SiO$_2$, petroleum ether/ethyl acetate=12:1, R$_f$=0.37) affording the desired product 107 as a pale yellow oil (1.79 g, 81% yield). $^1$H-NMR (CDCl$_3$, 400 MHz) δ=8.02 (1H, d, J=2.13 Hz, H$^{h'}$), 7.66 (1H, d, J=2.18 Hz, H$^h$), 7.50 (1H, dd, J=2.13 Hz, 8.54 Hz, H$^{d'}$), 7.15 (1H, dd, J=2.25 Hz, 8.46 Hz, H$^d$), 6.92 (1H, d, J=12.92 Hz, H$^a$), 6.78-6.71 (2H, m, H$^{e/e'}$), 6.07 (1H, d, J=6.94 Hz, H$^{a'}$), 5.70 (1H, d, J=13.00 Hz, H$^b$), 5.09 (1H, d, J=6.98 Hz, H$^{b'}$), 3.86/3.85 (6H, s, H$^{i/i'}$), 3.77 (3H, s, H$^{j'}$), 3.66 (3H, s, H$^j$) ppm. $^{13}$C-NMR (CDCl$_3$, 101 MHz) δ=156.4 (C$^f$), 156.1 (C$^{f'}$), 148.5 (C$^a$), 147.3 (C$^{a'}$), 139.1 (C$^{h'}$), 136.1 (C$^h$), 131.3 (C$^c$), 131.0 (C$^{c'}$), 129.4 (C$^{d'}$), 126.3 (C$^d$), 111.2/110.7 (C$^{e/e'}$), 103.9 (C$^{b'}$), 103.4 (C$^b$), 86.5 (C$^g$), 86.0 (C$^{g'}$), 60.8 (C$^{j'}$), 56.7/56.6/56.5 (C$^{j/i'/i''}$) ppm. ESI-MS (m/z): 290.80 [M+H]$^+$.

2-(3-Iodo-4-methoxyphenyl)ethan-1-ol C$_9$H$_{11}$O$_2$I
(108)

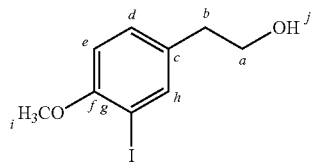

(E/Z)-2-Iodo-1-methoxy-4-(2-methoxyvinyl)benzene 107 (1.79 g, 6.17 mmol, 1.00 equiv.) was suspended in tetrahydrofuran (46 mL) and water (74 mL) before mercury acetate (2.18 g, 6.84 mmol, 1.10 equiv.) was added at 0° C. The reaction mixture was stirred at 0° C. for 30 min followed by the addition of a 50% aqueous potassium carbonate solution (30 mL) and sodium borohydride (942 mg, 24.90 mmol, 4.00 equiv.). After the reaction mixture was stirred at 0° C. for 2.5 h, the precipitate was filtered off and the filtrate was extracted with ethyl acetate (3×80 mL). The combined organic layers were dried over sodium sulfate and the solvent was removed under reduced pressure. The crude material was purified by column chromatography (SiO$_2$, petroleum ether/ethyl acetate=1:1, R$_f$=0.45) to obtain alcohol 108 as a yellow oil (1.36 g, 79% yield). $^1$H-NMR (CDCl$_3$, 400 MHz) δ=7.65 (1H, d, J=2.13 Hz, H$^h$), 7.16 (1H, dd, J=2.14 Hz, 8.35 Hz, H$^d$), 6.76 (1H, d, J=8.35 Hz, H$^e$), 3.85 (3H, s, H$^i$), 3.81 (2H, t, J=6.55 Hz, H$^a$), 2.76 (2H, t, J=6.53 Hz, H$^b$), 1.69 (1H, s, H$^j$) ppm. $^{13}$C-NMR (CDCl$_3$, 101 MHz) δ=157.0 (C$^f$), 139.9 (C$^h$), 132.9 (C$^c$), 130.2 (C$^d$), 111.1 (C$^e$), 86.2 (C$^g$), 63.7 (C$^a$), 56.5 (C$^i$), 37.8 (C$^b$) ppm. ESI-MS (m/z): 278.80 [M+H]$^+$.

3-Iodo-4-methoxyphenethyl acetate C$_{11}$H$_{13}$O$_3$I
(113)

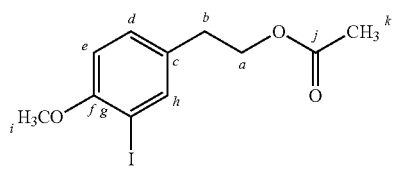

2-(3-Iodo-4-methoxyphenyl)ethan-1-ol 108 (1.04 g, 3.74 mmol, 1.00 equiv.) was dissolved in acetone (20 mL) and acetyl chloride (800 μL, 11.21 mmol, 3.00 equiv.) was added at 0° C. The reaction mixture was stirred at room temperature for 18 h before the solvent was removed under reduced pressure. The residue was dissolved in ethyl acetate (20 mL) and washed with saturated aqueous sodium bicarbonate solution (1×20 mL) and brine (1×20 mL). The organic layer was dried over sodium sulfate and the solvent was removed under reduced pressure. The crude material was purified by column chromatography (SiO$_2$, petroleum ether/ethyl acetate=3:1, R$_f$=0.54) to obtain acetate 113 as a yellow oil (1.07 g, 90% yield). $^1$H-NMR (CDCl$_3$, 400 MHz) δ=7.63 (1H, d, J=2.15 Hz, H$^h$), 7.15 (1H, dd, J=2.16 Hz, 8.39 Hz, H$^d$), 6.75 (1H, d, J=8.38 Hz, H$^e$), 4.22 (2H, t, J=7.01 Hz, H$^a$), 3.85 (3H, s, H$^i$), 2.83 (2H, t, J=7.01 Hz, H$^b$), 2.03 (3H, s, H$^k$) ppm. $^{13}$C-NMR (CDCl$_3$, 101 MHz) δ=171.1 (C$^j$), 157.1 (C$^f$), 139.9 (C$^h$), 132.2 (C$^c$), 130.0 (C$^d$), 111.0 (C$^e$), 86.1 (C$^g$), 64.9 (C$^a$), 56.5 (C$^i$), 33.8 (C$^b$), 21.1 (C$^k$) ppm. ESI-MS (m/z): 342.85 [M+Na]$^+$.

4-Hydroxy-3-iodophenethyl acetate C$_{10}$H$_{11}$O$_3$I
(114)

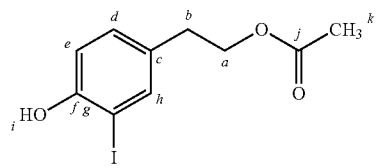

3-Iodo-4-methoxyphenethyl acetate 113 (588 mg, 1.87 mmol, 1.00 equiv.) was dissolved in dry dichloromethane (12 mL) under inert gas atmosphere and a solution of boron tribromide (445 μL, 4.69 mmol, 2.50 equiv.) in dry dichloromethane (12 mL) was added at −20° C. The reaction mixture was stirred for 2 h and partitioned between ethyl acetate (60 mL) and a 50% aqueous sodium bicarbonate solution (60 mL). The layers were separated and the aqueous layer was extracted with ethyl acetate (2×60 mL). The combined organic layers were washed with brine (1×180 mL) and dried over sodium sulfate. Evaporation of the solvent under reduced pressure and purification by column chromatography (SiO$_2$, petroleum ether/ethyl acetate=3:1, R$_f$=0.36) afforded phenol 114 as a yellow oil (602 mg, 92% yield). $^1$H-NMR (CDCl$_3$, 400 MHz) δ=7.51 (1H, d, J=2.08 Hz, H$^h$), 7.08 (1H, dd, J=2.05 Hz, 8.28 Hz, H$^d$), 6.91 (1H, d, J=8.29 Hz, H$^e$), 5.47 (1H, bs, H$^i$), 4.22 (2H, t, J=7.02 Hz, H$^a$), 2.83 (2H, t, J=6.99 Hz, H$^b$), 2.04 (3H, s, H$^k$) ppm. $^{13}$C-NMR (CDCl$_3$, 101 MHz) δ=171.2 (C$^j$), 153.8 (C$^f$), 138.5 (C$^h$), 132.0 (C$^c$), 130.8 (C$^d$), 115.1 (C$^e$), 85.6 (C$^g$), 65.0 (C$^a$), 33.8 (C$^b$), 21.1 (C$^k$) ppm. ESI-MS (m/z): 328.85 [M+Na]$^+$.

4-(3-Chloropropoxy)-3-iodophenethyl acetate C$_{13}$H$_{16}$O$_3$ICl

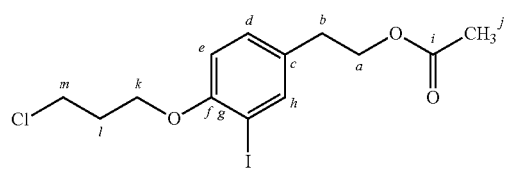 [SMILES: CC(=O)OCCc1ccc(OCCCCl)c(I)c1]

4-Hydroxy-3-iodophenethyl acetate 114 (330 mg, 1.08 mmol, 1.00 equiv.) was dissolved in acetone (17 mL) followed by the addition of 3-chloro-1-iodopropane (177 μL, 1.65 mmol, 1.53 equiv.) and cesium carbonate (702 mg, 2.15 mmol, 2.00 equiv.). The reaction mixture was stirred at 70° C. for 18 h before water (85 mL) was added. After an extraction with ethyl acetate (3×85 mL), the combined organic layers were washed with brine (1×215 mL) and dried over sodium sulfate. The solvent was removed under reduced pressure and the crude product was purified by column chromatography (SiO$_2$, petroleum ether/ethyl acetate=5:1, R$_f$=0.42) to give the title compound as a yellow oil (372 mg, 90% yield). $^1$H-NMR (CDCl$_3$, 400 MHz) δ=7.63 (1H, d, J=2.16 Hz, H$^h$), 7.13 (1H, dd, J=2.15 Hz, 8.33 Hz, H$^d$), 6.76 (1H, d, J=8.35 Hz, H$^e$), 4.22 (2H, t, J=6.99 Hz, H$^a$), 4.14 (2H, t, J=5.68 Hz, H$^k$), 3.84 (2H, t, J=6.33 Hz, H$^m$), 2.83 (2H, t, J=6.99 Hz, H$^b$), 2.23 (2H, quint, J=6.00 Hz, H$^i$), 2.03 (3H, s, H$^j$) ppm. $^{13}$C-NMR (CDCl$_3$, 101 MHz) δ=171.1 (C$^j$), 156.1 (C$^f$), 139.8 (C$^h$), 132.5 (C$^c$), 130.0 (C$^d$), 112.2 (C$^e$), 86.8 (C$^g$), 65.6 (C$^k$), 64.9 (C$^a$), 41.8 (C$^m$), 33.8 (C$^b$), 32.3 (C$^i$), 21.1 (C$^l$) ppm. ESI-MS (m/z): 404.80 [M+Na]$^+$.

2-(4-(3-Chloropropoxy)-3-iodophenyl)ethan-1-ol C$_{11}$H$_{14}$O$_2$ICl (117)

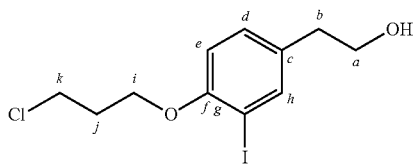 [SMILES: OCCc1ccc(OCCCCl)c(I)c1]

4-(3-Chloropropoxy)-3-iodophenethyl acetate (189 mg, 0.49 mmol, 1.00 equiv.) was dissolved in methanol (9 mL) before potassium carbonate (650 mg, 4.70 mmol, 9.60 equiv.) was added. The reaction mixture was stirred at room temperature for 3 h and was partitioned between water (60 mL) and dichloromethane (60 mL) followed by layer separation. The aqueous layer was extracted with dichloromethane (2×60 mL) and the combined organic layers were washed with brine (1×180 mL) and dried over sodium sulfate. The solvent was removed under reduced pressure to obtain alcohol 117 as a yellow oil (175 mg, quant.) which was used directly in the next step. $^1$H-NMR (CDCl$_3$, 400 MHz) δ=7.65 (1H, d, J=2.15 Hz, H$^h$), 7.16 (1H, dd, J=2.12 Hz, 8.32 Hz, H$^d$), 6.77 (1H, d, J=8.36 Hz, H$^e$), 4.14 (2H, t, J=5.72 Hz, H$^j$), 3.87-3.78 (4H, m, H$^{a,k}$), 2.77 (2H, t, J=6.48 Hz, H$^b$), 2.27 (2H, quint, J=6.00 Hz, H$^i$) ppm. $^{13}$C-NMR (CDCl$_3$, 101 MHz) δ=156.1 (C$^f$), 139.9 (C$^h$), 133.3 (C$^c$), 130.2 (C$^d$), 112.3 (C$^e$), 87.0 (C$^g$), 65.7 (C$^j$), 63.7 (C$^a$), 41.8 (C$^k$), 37.9 (C$^b$), 32.3 (C$^i$) ppm. ESI-MS (m/z): 362.80 [M+Na]$^+$.

tert-Butyl (((tert-butoxycarbonyl)imino)(3,5-dimethyl-4-oxo-1,3,5-triazinan-1-yl)methyl)(4-(3-chloropropoxy)-3-Iodophenethyl)carbamate C$_{27}$H$_{41}$N$_5$O$_6$ICl (121)

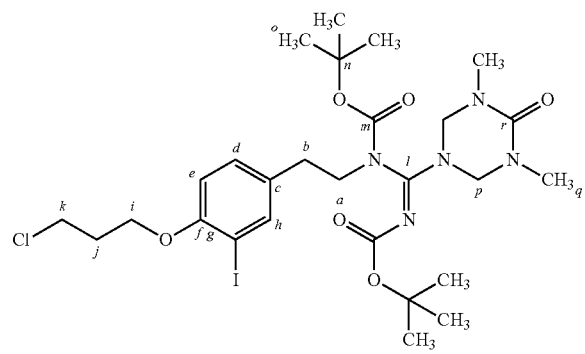 [SMILES: CN1CN(/C(=N/C(=O)OC(C)(C)C)N(CCc2ccc(OCCCCl)c(I)c2)C(=O)OC(C)(C)C)CN(C)C1=O]

2-(4-(3-Chloropropoxy)-3-iodophenyl)ethan-1-ol 117 (160 mg, 0.47 mmol, 1.00 equiv.), triphenylphosphine (185 mg, 0.71 mmol, 1.51 equiv.) and 24 (175 mg, 0.47 mmol, 1.00 equiv.) were dissolved in dry tetrahydrofuran (23 mL) under inert gas atmosphere. DIAD (140 µL, 0.71 mmol, 1.51 equiv.) was added at 0° C. and the reaction mixture was stirred at room temperature for 18 h. The solvent was removed under reduced pressure and the residue was partitioned between water (20 mL) and ethyl acetate (20 mL) followed by layer separation. The aqueous layer was extracted with ethyl acetate (2×20 mL) and the combined organic layers were washed with brine (1×60 mL) and dried over sodium sulfate. Evaporation of the solvent under reduced pressure and purification by column chromatography (SiO$_2$, petroleum ether/acetone/ethyl acetate=5:3:1, R$_f$=0.38) gave the title compound 121 as a pale green oil (272 mg, 83% yield). $^1$H-NMR (CDCl$_3$, 400 MHz) δ=7.61 (1H, d, J=1.81 Hz, H$^h$), 7.12 (1H, dd, J=1.71 Hz, 8.25 Hz, H$^d$), 6.74 (1H, d, J=8.31 Hz, H$^e$), 4.50 (4H, bs, H$^p$), 4.16-4.07 (3H, m, H$^l$), 3.82 (2H, t, J=6.25 Hz, H$^k$), 3.57 (2H, bs, H$^a$), 2.88-2.80 (8H, m, H$^{b,q}$), 2.26 (2H, quint, J=5.96 Hz, H$^j$), 1.48 (9H, s, H$^o$), 1.47 (9H, s, H$^o$) ppm. $^{13}$C-NMR (CDCl$_3$, 101 MHz) δ=156.3 (C$^{f,r}$), 152.4/151.3 (C$^{l,m}$), 139.6 (C$^h$), 132.5 (C$^c$), 129.9 (C$^d$), 112.3 (C$^e$), 87.0 (C$^g$), 83.1/80.9 (C$^n$), 65.7 (C$^i$), 61.2 (C$^p$), 49.0 (C$^a$), 41.7 (C$^k$), 33.2 (C$^q$), 33.1 (C$^b$), 32.2 (C$^j$), 28.3/28.2 (C$^o$) ppm. ESI-MS (m/z): 694.20 [M+H]$^+$, 716.05 [M+Na]$^+$.

tert-Butyl (((tert-butoxycarbonyl)imino)(3,5-dimethyl-4-oxo-1,3,5-triazinan-1-yl)methyl)(3-odo-4-(3-odopropoxy)phenethyl)carbamate C$_{27}$H$_{41}$N$_5$O$_6$I$_2$ (122)

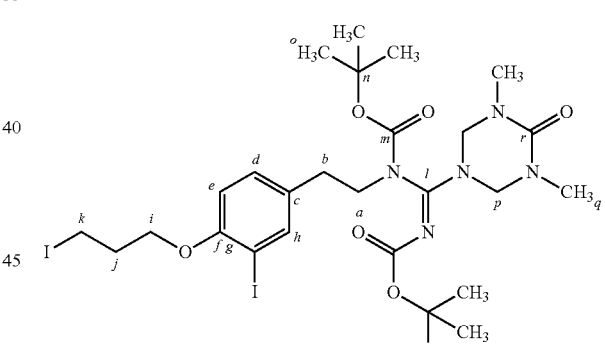

121 (236 mg, 0.34 mmol, 1.00 equiv.) was dissolved in acetone (30 mL) and sodium iodide (510 mg, 3.40 mmol, 10.00 equiv.) was added. The reaction mixture was stirred at 70° C. for 18 h and the solvent was removed under reduced pressure. Since LC-MS indicated incomplete conversion of the starting material, an additional amount of sodium iodide (816 mg, 5.44 mmol, 16.00 equiv.) was added. The reaction mixture was stirred at 70° C. for another day. After adding another amount of sodium iodide (816 mg, 5.44 mmol, 16.00 equiv.), the reaction mixture was stirred at 70° C. for additional 18 h before partitioning between water (15 mL) and diethyl ether (15 mL) followed by layer separation. The aqueous layer was extracted with diethyl ether (2×15 mL) and the combined organic layers were washed with brine (1×45 mL) and dried over sodium sulfate. The solvent was removed under reduced pressure to obtain iodide 122 as a yellow oil (221 mg, 83% yield) which was used directly in the next step. $^1$H-NMR (CDCl$_3$, 400 MHz) δ=7.62 (1H, d, J=2.16 Hz, H$^h$), 7.13 (1H, dd, J=2.22 Hz, 8.31 Hz, H$^d$), 6.75 (1H, d, J=8.33 Hz, H$^e$), 4.51 (4H, bs, H$^p$), 4.05 (3H, t, J=5.69 Hz, H$^i$), 3.58 (2H, bs, H$^a$), 3.46 (3H, t, J=6.60 Hz, H$^k$), 2.90-2.75 (8H, m, H$^{b,q}$), 2.32-2.24 (2H, m, H$^j$), 1.48 (9H, s, H$^o$), 1.47 (10H, s, H$^o$) ppm. $^{13}$C-NMR (CDCl$_3$, 101 MHz) δ=157.0 (C$^r$), 156.2 (C$^f$), 152.3/151.1 (C$^{l,m}$), 139.6 (C$^h$), 132.6 (C$^c$), 129.8 (C$^d$), 112.4 (C$^e$), 87.0 (C$^g$), 83.1/81.0 (C$^n$), 68.7 (C$^i$), 61.2 (C$^p$), 49.0 (C$^a$), 33.3 (C$^q$), 33.1 (C$^b$), 32.9 (C$^j$), 28.3/28.2 (C$^o$), 3.1 (C$^k$) ppm. ESI-MS (m/z): 786.00 [M+H]$^+$, 807.90 [M+Na]$^+$.

3-(4-(2-(N,N'-Bis(tert-butoxycarbonyl)-3,5-dimethyl-4-oxo-1,3,5-triazinane-1-carboximidamido)ethyl)-2-iodophenoxy)propyl 4-methylbenzenesulfonate C$_{34}$H$_{48}$N$_5$O$_9$SI (123)

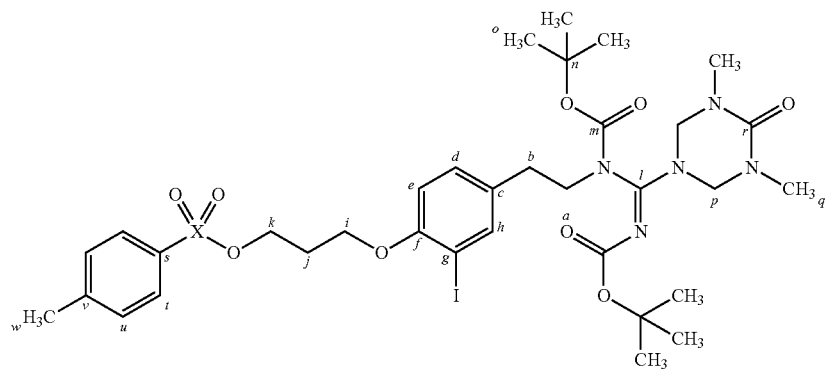

122 (191 mg, 0.24 mmol, 1.00 equiv.) was dissolved in acetonitrile (10 mL) and silver p-toluenesulfonate (340 mg, 1.22 mmol, 5.00 equiv.) was added. The reaction mixture was stirred in darkness at room temperature for 72 h before the solvent was removed under reduced pressure. The residue was partitioned between water (15 mL) and ethyl acetate (15 mL) followed by layer separation. The aqueous layer was extracted with ethyl acetate (2×15 mL) and the combined organic layers were washed with brine (1×40 mL) and dried over sodium sulfate. Evaporation of the solvent under reduced pressure and purification by column chromatography by column chromatography (SiO$_2$, petroleum ether/acetone/ethyl acetate=6:3:1, R$_f$=0.33) afforded the target compound 123 as a colourless foam (113 mg, 56% yield). $^1$H-NMR (CDCl$_3$, 400 MHz) δ=7.75 (2H, d, J=8.33 Hz, H$^t$), 7.58 (1H, d, J=2.06 Hz, H$^h$), 7.23 (2H, d, J=8.32 Hz, H$^u$), 7.10 (1H, dd, J=2.04 Hz, 8.33 Hz, H$^d$), 6.62 (1H, d, J=8.22 Hz, H$^e$), 4.52 (3H, bs, H$^p$), 4.31 (2H, t, J=6.02 Hz, H$^k$), 3.96 (2H, t, J=5.78 Hz, H$^i$), 3.56 (2H, bs, H$^a$), 2.88-2.79 (8H, m, H$^{b,q}$), 2.36 (3H, s, H$^w$), 2.19-2.10 (2H, m, H$^j$), 1.48 (9H, s, H$^o$), 1.47 (9H, s, H$^o$) ppm. $^{13}$C-NMR (CDCl$_3$, 101 MHz) δ=157.0 (C$^r$), 156.0 (C$^f$), 152.3/151.0 (C$^{l,m}$), 144.9 (C$^v$), 139.6 (C$^h$), 132.9 (C$^s$), 132.5 (C$^c$), 130.0 (C$^u$), 129.7 (C$^d$), 127.9 (C$^t$), 112.1 (C$^e$), 86.8 (C$^g$), 83.0/81.0 (C$^n$), 67.2 (C$^k$), 64.4 (C$^i$), 61.2 (C$^p$), 49.1 (C$^a$), 33.3 (C$^d$), 33.2 (C$^b$), 29.0 (C$^j$), 28.3/28.2 (C$^o$), 21.8 (C$^w$) ppm. ESI-MS (m/z): 830.10 [M+H]$^+$, 852.05 [M+Na]$^+$.

Radiochemistry

Radiofluorination was performed using K$^{18}$F to replace the tosylate group of precursor 123 with $^{18}$F. By the addition of 6N HCl, cleavage of the boc groups and the triazinanone moiety was achieved (FIG. 6). The desired radioactive labelled compound $^{18}$F-37 was obtained with an overall radiochemical yield of 22% (decay corrected) and >99% radiochemical purity.

Competitive Binding/Cell Uptake Studies

SK-N-SH cells expressing NET were cultivated according to the instructions from the supplier (Sigma-Aldrich Chemie GmbH, Munich, Germany). The cells were transferred to a 12 well plate and incubated in 1 mL EMEM while reaching 2×10$^5$ cells/well density the day for testing. The medium was removed, and the cells were washed with 1 mL EMEM. A solution of $^{18}$F-AF78 (3.7 kBq) in EMEM (700 μL) was added to each well with or without inhibitors (NE, MHPG, cold AF78 each with a final concentration 100 nM, 1 μM, 10 μM and 100 μM, respectively; Desipramine 10 μM). The plate was incubated for 60 min at 37° C. The cells were washed with ice-cold PBS buffer (1 mL×2) in order to remove unbound tracer. NaOH solution (0.1 N, 500 μL) was added to each well followed by the collection of cell pellet and the measurement in γ-counter (FH412, Frieseke & Höpfner, Erlangen, Germany) using differential energy windows (±20%) for $^{18}$F and $^{131}$I.

Cold, i. e. non-radioactive, reference compound AF78 of the compound according to the invention and the following compound 1

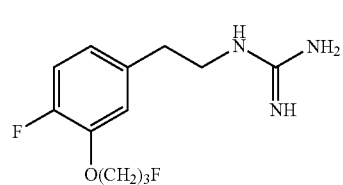

were synthesized. The compounds were tested in SK-N-SH cells expressing NET in order to evaluate their competitive binding affinity against $^{131}$I-MIBG. FIG. 7 shows the dose-response curves of $^{131}$I-MIBG uptake in SK-N-SH cells in the presence of increasing concentrations of the following non-radioactive compounds: NE (●), MHPG (■), cold reference 1 (=compound 1) (♦), cold reference 2 (=compound AF78) (▲). Results are expressed as percent of control MIBG uptake. IC50 of NE, MHPG, and cold reference 2 AF78 are 1.38±0.25 μM, 6.80±0.73 μM, and 2.57±1.37 μM, respectively. (IC50 of AF78 vs. MHPG p value<0.01)

NE and cold MIBG were used as references. As a result, cold reference 2 (AF78) could inhibit the cell uptake of $^{131}$I-MIBG in a concentration-dependent manner. In contrast, cold reference 1 was not able to block the uptake of $^{131}$I-MIBG even at the highest concentration tested. Inhibition was only 40% at 100 µM. This result provides a hint for a structure-activity relationship. The introduction of long alkyl chain at 3-position on the benzene ring seems not to be tolerated, whereas introduction at the 4-position seems to be well tolerated.

After successful radiolabeling, $^{18}$F-AF78 was also tested in SK-N-SH cells in order to check cell uptake. Antidepressant desipramine (DMI) was used as the inhibitor of NET. Results are shown in FIG. 8. The addition of DMI blocks cell uptake of tracers specifically transported by NET. The results show that 94% of the uptake of $^{18}$F-AF78 was inhibited by the addition of DMI compared to 87% of $^{131}$I-MIBG, as a reference.

To further confirm the tracer's binding affinity, $^{18}$F-labeled AF78 was used in competitive inhibition assay, to which different concentrations of NE, MHPG, and cold reference 2 (AF78) were added. FIG. 9 shows dose-response curves of $^{18}$F-AF78 uptake in SK-N-SH cells in the presence of increasing concentrations of the following non-radioactive compounds: NE (●), MHPG (■), and cold AF78 (▲). Results are expressed as percentage of control AF78 uptake. NE, MHPG, and cold AF78 could inhibit the uptake of $^{18}$F-AF78 at an IC50 value of 0.60±0.27, 0.85±0.63, and 2.68±0.83 µM, respectively. (IC50 of MHPG vs. AF78, p value<0.05). These results are in accordance with the outcomes achieved by using $^{131}$I-MIBG as a reference. Therefore, it further confirmed that the structural modification retained the property of being specifically taken up by NET as compared to the original reference and the clinically used tracer $^{131}$I-MIBG.

Ex Vivo Autoradiography and Tissue Counting Studies

Standard protocols and data analysis methods for non-invasive PET imaging of small animals have been established in the working group of the inventors (Rischpler C. et al., Eur J Nucl Med Mol Imaging. 2013; 40(7): 1077-83). Healthy male Wistar rats (Japan SLC, Inc., Japan) each weighing 200-250 g were used. The rats are anaesthetized with 2% isoflurane. 10-20 MBq of the tracer was administered via tail vein injection. Ten minutes after the tracer administration, the animals were immediately euthanized. Hearts, livers and blood were obtained for ex vivo analysis with autoradiography (Typhoon FLA 7000) and tissue counts with γ-counter (1480 WIZARD™ 3"). Following weight and decay correction of tissue counts, the heart to blood (H/B) and heart to liver (H/L) count ratio were calculated, respectively. For autoradiography, the rats were first injected via tail vein either with or without (control) NET blocker phenoxynezamine 50 mg/kg after anaesthesia. After 10 min, the tracer (10-20 MBq) was administered. The hearts were harvested 10 min later, frozen, and cut into 20 µm short axis slices using a cryostat (Cryotome FSE, Thermo Fisher Scientific). To obtain the distribution of the tracer, autoradiography plates (Fuji SR-type image plate, Fujifilm Corporation, Tokyo, Japan) were exposed to the short axis slices immediately for 18 h and thereafter imaged using a digital autoradiographic system (Typhoon FLA 7000).

Cardiac Imaging Studies in Rats and Monkeys

In an autoradiography study of left ventricular short axis (LVSA) slices from rats, $^{18}$F-AF78 showed homogeneous tracer uptake throughout the left ventricular walls in the healthy myocardium. The result is shown in FIG. 10. $^{18}$F-AF78 demonstrated an even distribution throughout the myocardium (control), which could be inhibited by a pretreatment with phenoxybenzamine (PhB, 50 mg/kg i.v. injection) 10 min before tracer injection. A lack of delineation of the right ventricular wall might be due to its thinness and the slicing position.

An ex vivo tissue counting study showed that the tracer has a reasonable uptake in the heart as demonstrated in both Heart-to-Blood (H/B) and Heart-to-Liver (H/L) ratio counting 12.54 and 6.14, respectively. This uptake could be specifically blocked by PhB (50 mg/kg) and led to approximately 6 fold decline in the H/B ratio and 5 fold decline in the H/L ratio, counting 2.41 and 1.30, respectively. Results of the tissue distribution study are shown in FIG. 11. The columns are the mean value of 2 rats. Data were determined 10 min post injection. Y-axis represents the heart/tissue distribution ratio. Both the Heart-to-Blood ratio (H/B) and the Heart-to-Liver (H/L) ratio decreased significantly after pretreatment with PhB (50 mg/kg, NET blockade) 10 min before tracer injection. In comparison, according to Raffel, D. et al., J. Nucl. Med. 2017, 58 (Suppl 1): 96 MHPG and PHPG show tissue concentration ratios at a time frame of 50-60 min imaging as follows: MHPG with H/B 3.6 and H/L 2.3; PHPG with 5.4 and 1.1, respectively. Therefore, the low liver uptake of $^{18}$F-AF78 facilitates the possibility of evaluating the inferior wall activity of the heart. This highly specific cardiac uptake shows that $^{18}$F-AF78 is an almost ideal PET imaging of the heart.

Cardiac PET Imaging in Animals

Rats were maintained anaesthetized during the whole experiment by 2% isoflurane. All scans were obtained using a dedicated small-animal PET system (microPET FOCUS 120, SIEMENS, Germany). The PET imaging protocol was designed to assess the systemic and myocardial tracer distribution of $^{18}$F-AF78. Shortly before the injection of 10-20 MBq of $^{18}$F-AF78 via the tail vein, a dynamic PET scan was initiated. In order to evaluate the cardiac uptake mechanism of the tracer, rats were pretreated with phenoxybenzamine (50 mg/kg intravenously, Sigma-Aldrich, Tokyo, Japan). Ten minutes after the pretreatment, 10-20 MBq of $^{18}$F-AF78 was administered via the tail vein. A 10 min dynamic PET session was started shortly before the tracer injection. PET image was acquired in list-mode format. The data were sorted into 3-dimensional sonograms, which were then rebind with a Fourier algorithm to reconstruct dynamic images using a 2-dimensional ordered-subset expectation maximization (OSEM) algorithm. All images were corrected for $^{18}$F decay, random, and dead time; correction for attenuation was not performed (Higuchi JNM 2013). The obtained PET images were analyzed with the public domain tool AMIDE imaging software (A Medical Imaging Data Examiner, version 1.01).

Systemic distribution of $^{18}$F-AF78 $^{18}$F-37 in the healthy rat myocardium by in vivo PET with (NET Blockade) or without (No pretreatment) pretreatment with NET blocker PhB (50 mg/kg iv injection) 10 min before the tracer injection is shown in FIGS. 12 and 13. The static PET images show homogeneous and clear tracer uptake throughout the left ventricular wall. Pretreatment with NET blocker PhB (50 mg/kg, intravenously via tail vein) significantly decreased the myocardial tracer uptake (FIGS. 12 and 13, NET Blockade).

For control, Cynomolgus monkey (male, 5.3 kg) was maintained anaesthetized during the imaging study using 3.3% sebofluorane. Shortly before receiving an intravenous injection of the tracer (44 MBq), a 120 min dynamic PET session was started. In addition, to investigate the inhibition of cardiac neuronal uptake-1, DMI (1 mg/kg, iv.) was injected to Cynomolgus monkey (female, 5.6 kg) 10 min before the tracer (18.2 MBq) injection and PET assessment started. PET was conducted using a PCA-2000A positron scanner (Toshiba Medical Systems Corporation, Otawara, Japan). Sinograms were collected with the following pattern: 10 sec×12, 30 sec×6, 300 sec×23. The tissue uptake was determined as arbitrary unit (A.U.), from which a time-activity curves of different organs were generated.

A tissue bio-distribution consistent with that observed in rat could be observed with clear long term and stable cardiac uptake during the total 120 min scan whereas uptake in adjacent liver and lungs was low. Representative time activity curves derived from $^{18}$F-AF78 dynamic images in control and sympathetic nerve blocked monkey were generated from the scanning data. The time activity curves expressed in arbitrary unit, A.U. versus time in minutes are shown FIG. 14. $^{18}$F-AF78 cardiac uptake showed a high tracer activity after the first washout and maintained activity throughout the entire 120 min scan time. The pretreatment with uptake-1 inhibitor DMI (1 mg/kg, iv) 10 min before the tracer injection markedly reduced the heart uptake level, which dropped almost instantly to the same level as in blood. In the control, activity in the liver reached a peak a little while after the tracer injection, then decreased slowly to blood level after 60 min. The results show a stable long-term cardiac specific uptake with favorable Heart/Blood and Heart/Liver ratios. Tracer uptake in the liver was not affected by pretreatment with DMI.

Further biodistribution studies were performed in rats (n=4) 10 min after injection of the tracer $^{18}$F-37 demonstrating favourable heart-to-blood (H/B, approx. 6:1) and heart-to-liver (H/L, approx. 2:1) ratios (FIG. 15, right panel). Heart-to-muscle ratios (H/M) were very high with a value of approx. 12:1. Time activity curves indicated stable long term cardiac uptake (expressed in arbitrary unit, A.U.) which is displayed in FIG. 15 (left panel). 16 MBq of tracer activity was injected.

Static PET images of cardiac uptake of $^{18}$F-AF78 in healthy rats, rabbits, pigs and monkeys (FIG. 16) show that $^{18}$F-AF78 works in all of these species such that it can be assumed that it works in all mammals including humans.

A further biodistribution study with $^{18}$F-AF78 in monkey has been conducted. Results calculated as SUV (standardized uptake value) are shown in FIG. 17. The results show a stable cardiac uptake along with fast blood pool washout and relative fast liver uptake washout. The liver uptake is decreasing and is lower than cardiac uptake 35 min after tracer administration.

A kinetic study has been performed with $^{18}$F-AF78 in monkeys' hearts. The results confirmed the specific uptake of $^{18}$F-AF78 via NET and stable vesicular storage mechanism in the sympathetic nerve terminals. When injected 10 min before the tracer administration, NET blocker desipramine (DMI) specifically blocked the tracer uptake with significant difference (p<0.0001) compared to control (FIG. 18, upper panel). In contrast, when performing DMI chase (injected 10 min after the tracer administration), no difference can be seen compared to control group (FIG. 18, middle panel). Furthermore, a continuous tyramine (TYR) chase was applied after tracer administration. Tyramine is known as agent causing a catecholamine release thus enhancing tracer washout. The cardiac uptake of $^{18}$F-AF78 decreased considerable. Decrease was statistically significant (p<0.005) compared to control group (FIG. 18, lower panel).

Statistical Analysis

All results are displayed as mean±SD. The two-tailed paired Student t-test was used to compare differences between two dependent groups, and the two-tailed independent Student t-test for differences between independent groups. Multiple group comparisons were performed using analysis of variance (ANOVA). A p value of less than 0.05 was assumed to be statistically significant. Statistical analysis was performed with StatMate III (ATMS Co., Ltd.).

The Meaning of Abbreviations Used in this Specification is as Follows:

DIAD, diisopropyl azodicarboxylate; DIPEA, N,N-diisopropylethylamine; DMF, N,N-dimethylformamide; DMI, desipramine; $^{11}$C-HED, $^{11}$C-(−)-m-hydroxyephedrine; iv, intravenously; $^{18}$F-MHPG, $^{18}$F-4-fluoro-3-hydroxyphenethylguanidine; $^{123/131}$I-MIBG, $^{123/131}$I-meta-iodobenzylguanidine; NE, norepinephrine; NET, norepinephrine transporter; PET, positron emission tomography; PhB, phenoxybenzamine; $^{18}$F-PHPG, $^{18}$F-3-fluoro-4-hydroxyphenethylguanidine; SPECT, single photon emission computed tomography; THF, tetrahydrofuran

The invention claimed is:

1. A compound according to following formula

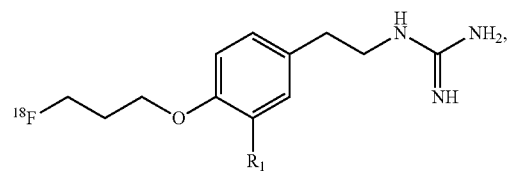

wherein $R_1$ is F.

2. A method, comprising:

administering the compound according to claim 1.

3. The method according to claim 2, wherein the compound is administered to a living human or animal body suspected of having a disorder in generation, degradation, distribution, or function of norepinephrine transporter (NET).

4. The method according to claim 3, wherein after administration of the compound, the living human or animal body is scanned with Positron Emission Tomography (PET).

5. The method according to claim 4, wherein the disorder in generation, degradation, distribution, or function of NET is associated with a cardiovascular disease, a dysregulated blood pressure, a renal disorder, a neuroendocrine tumor disease, or Parkinson's disease.

6. A method for synthesizing the compound according to claim 1, comprising:

a) removing the methyl group of the following compound 14

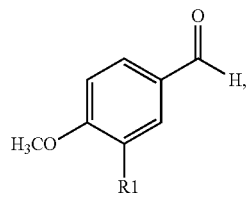

to receive the following compound 15

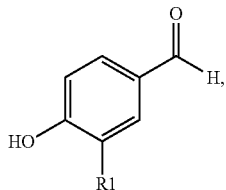

wherein R1 is a halogen residue, b) performing a chloroalkylation of compound 15 with 1-chloro-3-iodopropane, to receive the following compound 25

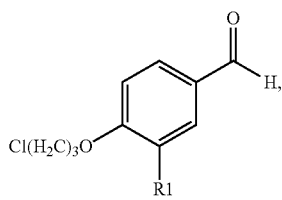

c) performing a Wittig reaction with compound 25 with a (methoxymethyl)triphenylphosphonium halide and potassium tert-butoxide or sodium hydride, to receive the following compound 26

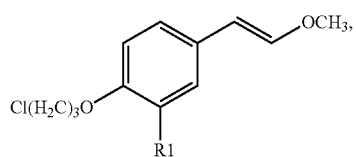

d) reducing compound 26 in a two-step one pot reaction by addition of mercury acetate to allow formation of an intermediate followed by addition of an alkali metal borohydride, to receive the following compound 28

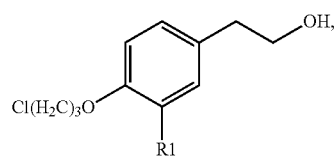

e) performing a Mitsunobu reaction with compound 28 in the presence of triphenylphosphine, an azodicarboxylate, and the following compound 24

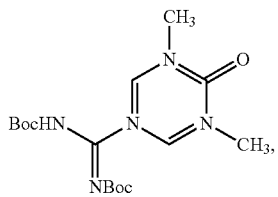

to receive the following compound 29

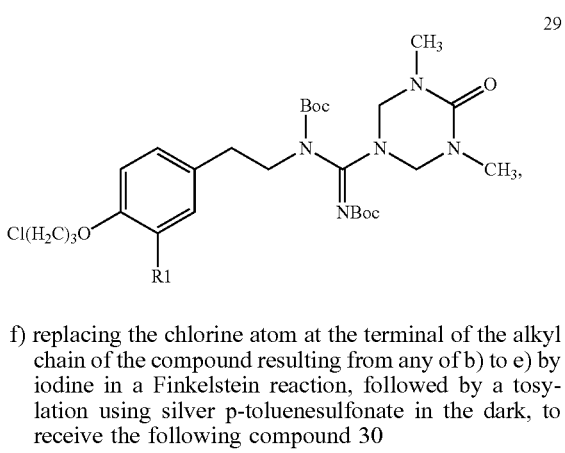

f) replacing the chlorine atom at the terminal of the alkyl chain of the compound resulting from any of b) to e) by iodine in a Finkelstein reaction, followed by a tosylation using silver p-toluenesulfonate in the dark, to receive the following compound 30

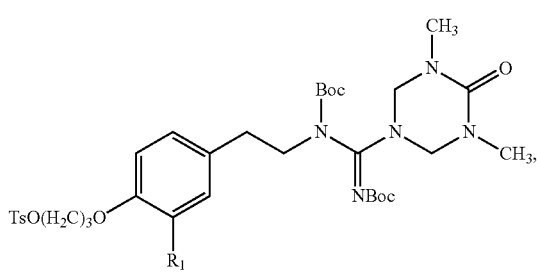

wherein a)-f) are performed in any order to obtain the compound 30, and g) radiolabeling compound 30 by a nucleophilic substitution using an alkali metal salt of $^{18}F$ followed by deprotection under acidic condition at a temperature of at least 70° C., to receive the following compound

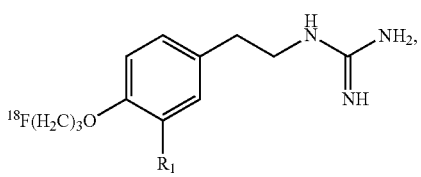

wherein the halogen residue is an F or an I residue.

7. The method according to claim 6, wherein the (methoxymethyl)triphenylphosphonium halide of c) is (methoxymethyl)triphenylphosphonium chloride.

8. The method according to claim 6, wherein the azodicarboxylate of e) is diethyl azodicarboxylate (DEAD) or diisopropyl azodicarboxylate (DIAD).

9. The method according to claim 6, wherein the alkali metal borohydride of d) is sodium borohydride or potassium borohydride.

10. The method according to claim 6, wherein the alkali metal salt of $^{18}F$ used in g) is $K^{18}F$.

11. The method according to claim 6, wherein the deprotection under acidic condition of g) is performed at a temperature of at most 100° C.

12. The method according to claim 6, wherein synthesis of compound 24 comprises:
h) reacting benzyl carbamate, N,N'-dimethylurea, and water at a temperature of at least 80° C., to receive the following compound 23

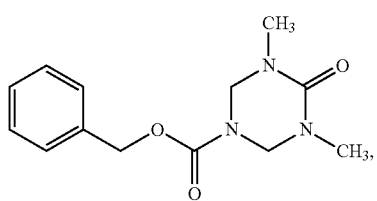

i) reacting compound 23 with hydrogen catalyzed by palladium on activated charcoal, to receive compound 22

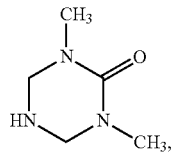

j) reacting compound 22 with the following compound 13

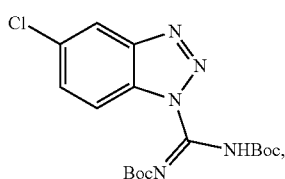

in the presence of N,N-diisopropylethylamine (DIPEA) to receive compound 24,
wherein Boc is a tert-butoxycarbonyl protecting group.

13. The method according to claim 12, wherein compound 13 of j) is synthesized by reacting 1,3-bis(tert-butoxycarbonyl)-2-methyl-2-thiopseudourea and 5-chlorobenzotriazole in the presence of mercury (II) chloride ($HgCl_2$).

14. The compound according to claim 1, wherein cell uptake of the compound is blocked by the presence of an antidepressant desipramine (DMI).

15. The compound according to claim 1, wherein cell uptake of the compound is blocked by the presence of an antidepressant desipramine (DMI), compared to $^{131}I$-meta-iodobenzylguanidine ($^{131}I$-MIBG).

16. The compound according to claim 1, having >99% radiochemical purity.

17. The compound according to claim 1, wherein the compound has a binding affinity to norepinephrine transporter (NET) equal to or better than $^{131}I$-meta-iodobenzylguanidine ($^{131}I$-MIBG).

18. The compound according to claim 1, wherein the compound is inhibited by phenoxybenzamine (PhB) or a pretreatment with phenoxybenzamine (PhB).

* * * * *